United States Patent
Aladahalli et al.

(10) Patent No.: US 11,712,224 B2
(45) Date of Patent: Aug. 1, 2023

(54) METHOD AND SYSTEMS FOR CONTEXT AWARENESS ENABLED ULTRASOUND SCANNING

(71) Applicant: GE Precision Healthcare LLC, Milwaukee, WI (US)

(72) Inventors: Chandan Kumar Mallappa Aladahalli, Bangalore (IN); Krishna Seetharam Shriram, Bangalore (IN); Vikram Melapudi, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 871 days.

(21) Appl. No.: 16/600,394

(22) Filed: Oct. 11, 2019

(65) Prior Publication Data
US 2021/0106314 A1    Apr. 15, 2021

(51) Int. Cl.
| | | |
|---|---|---|
| A61B 8/08 | (2006.01) |
| G06T 7/00 | (2017.01) |
| G06V 20/20 | (2022.01) |
| G06V 10/764 | (2022.01) |
| G06V 10/82 | (2022.01) |
| G06V 10/26 | (2022.01) |

(52) U.S. Cl.
CPC .......... *A61B 8/5215* (2013.01); *G06T 7/0012* (2013.01); *G06V 10/26* (2022.01); *G06V 10/764* (2022.01); *G06V 10/82* (2022.01); *G06V 20/20* (2022.01); *G06T 2207/10132* (2013.01)

(58) Field of Classification Search
CPC ...... A61B 8/5215; G06V 20/20; G06V 10/82; G06V 10/26; G06V 10/764; G06T 7/0012; G06T 2207/10132
See application file for complete search history.

(56) References Cited

U.S. PATENT DOCUMENTS

| | | | |
|---|---|---|---|
| 2008/0221446 A1* | 9/2008 | Washburn ............ | A61B 8/4254 600/437 |
| 2010/0322489 A1* | 12/2010 | Tizhoosh .................. | G06T 7/12 345/157 |
| 2011/0075902 A1* | 3/2011 | Song ........................ | G06T 7/66 382/128 |
| 2011/0295118 A1* | 12/2011 | Okamura ............... | A61B 8/469 600/440 |
| 2020/0323512 A1* | 10/2020 | Ng ........................ | A61B 8/467 |

\* cited by examiner

*Primary Examiner* — Chao Sheng
(74) *Attorney, Agent, or Firm* — McCoy Russell LLP

(57) ABSTRACT

Various methods and systems are provided for generating a context awareness graph for a medical scan image. In one example, the context awareness graph includes relative size and relative position annotations with regard to one or more internal anatomical features in the scan image to enable a user to determine a current scan plane and further, to guide the user to a target scan plane.

15 Claims, 11 Drawing Sheets

METHOD AND SYSTEMS FOR CONTEXT AWARENESS ENABLED ULTRASOUND SCANNING

FIELD

Embodiments of the subject matter disclosed herein relate to medical imaging modalities, particularly to systems and methods for ultrasound imaging.

BACKGROUND

Medical imaging systems are often used to probe internal features and obtain internal physiological information of a subject, such as a patient. For example, a medical imaging system may be used to obtain scan images of the bone feature, the brain, the heart, the lungs, and various other features of a subject. Medical imaging systems may include ultrasound systems, magnetic resonance imaging (MRI) systems, computed tomography (CT) systems, x-ray systems, and various other imaging modalities. The scan image may show several anatomical regions, one or more of which may be evaluated during a medical scan.

BRIEF DESCRIPTION

In one embodiment, a method for a medical imaging processor, comprises: acquiring a medical scan image; identifying one or more internal features in the medical scan image; generating a context awareness graph based on relative sizes and relative positions of the one or more internal features; and displaying the context awareness graph on a display portion of a user interface communicatively coupled to the medical imaging processor; wherein the context awareness graph includes a relative position annotation and a relative size annotation for each of the one or more internal features identified in the medical scan image.

In this way, a context awareness graph for a scan image produced during a medical scan provides internal feature information and relationship between the internal features visible in the scan image. Thus, the context awareness graph helps the user to locate the scan plane in a human anatomy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
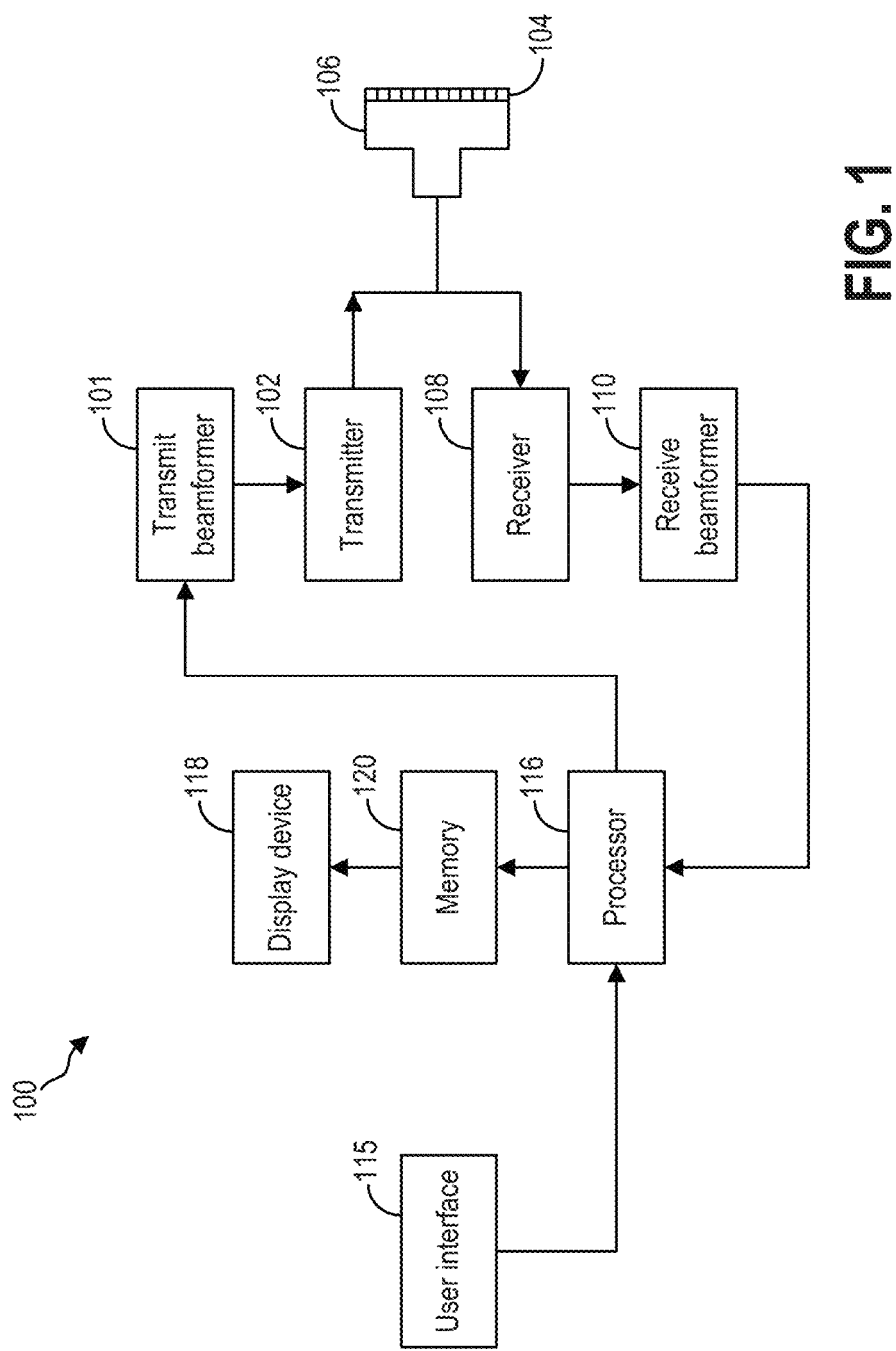
FIG. 1 shows a block diagram of an exemplary embodiment of an ultrasound system.

The following description relates to various embodiments for enabling context awareness of one or more internal features, such as anatomical features, in a medical scan image. For example, during an ultrasound scan, a scan image displayed to the user may show one or more internal anatomical features. A user may adjust the ultrasound probe based on the displayed image to arrive at a desired scan plane (alternatively referred to herein as target scan plane) to evaluate the internal features. In order to arrive at the target scan plane, the user may need to interpret the displayed scan image to identify the visible internal features in the current scan plane, visualize the current scan plane within the larger human anatomy, and determine the direction for moving the probe.

Previous approaches have employed artificial intelligence based machine learning approaches to learn the appearance of various anatomical features in a scan image and display a segmentation graph identifying the visible internal features in an ultrasound scan image. However, the segmentation graph merely provides identification of the internal features. An operator may not be able to visualize the scan plane with respect to the entire human anatomy, and as a result, may move the probe in a direction away from the target scan plane. Consequently, it may take a longer time to reach the target scan plane. Furthermore, the operator may not correctly identify the target scan plane even while imaging at the target scan plane, or arrive at the target scan plane during the scan. As a result the quality of evaluation of the internal features may be reduced even with the segmentation graph providing identification information of the anatomical features visible in the scan image.

Thus, in order to improve quality of ultrasound imaging and reduce time taken to perform the ultrasound scan, the ultrasound scanning may be performed in a context awareness mode, wherein a context awareness graph for an ultrasound scan image on display may be generated and displayed to the user. In the context awareness graph, relative sizes and relative positions of the visible internal features (that is, internal features visible in the scan image) are annotated. Specifically, each internal feature is represented by a node (e.g., circular node) with node sizes (e.g. area, or diameter in case of circular nodes) depicting relative size of the internal feature, and positions of the nodes on the graph depicting relative positions of the internal features on the scan image. Thus, the context awareness graph may include one or more nodes with each node indicating an internal feature in the scan image and an overall shape of the context awareness graph depicting relative positions of the internal features. Further, the context awareness graph may include segments depicting edges of the graph, where each segment connects at least two nodes. The segments may indicate one or more of relative distances and relative angular positions between the nodes they connect, and thus indicate one or more of relative distances and angular positions between the internal features represented by the connected nodes. For example, a length of each segment may be based on relative distances between the two nodes and thus, indicate relative distance between the corresponding internal features represented by the two nodes.

In this way, a context awareness graph may provide relative size and relative position information of one or more internal features in a scan image to an operator. Further, the context awareness graph may be generated in real-time as the imaging system acquires and processes scan images, which enables the operator to more clearly identify and visualize the changes in relative size and relative positions of the internal features during the scan.

Further, during an ultrasound scan, when moving the probe from a current scan plane to a target scan plane, shape of the context awareness graph changes based on the relative sizes, relative positions, and visibility of the internal features in the scan direction (e.g., graph shape may change from a triangle to a line), which may provide an indication to the user if the probe is moving towards the target scan plane. In this way the context awareness graph provides a visual feedback to the operator. The visual feedback provided by the context awareness graph may be utilized independently of other feedback systems, such as haptic feedback. Thus, the context awareness graph may reduce the need for additional sensors on the probe, which in turn may reduce the bulkiness of the system, and reduce manufacturing, system maintenance, and diagnostic costs.

Furthermore, as the context awareness graphs enables the operator to more clearly interpret the relative size and position changes to the internal features in real-time scan images during a scan, efficiency and accuracy of the scan is improved.

Further still, the context awareness graph may be utilized for guidance and coaching a novice user to interpret the scan image, determine if the user is moving toward the target scan plane, and correctly identify the target scan plane with improved efficiency and accuracy, without the use of sensors coupled to the probe or the patient.

Figure 2:
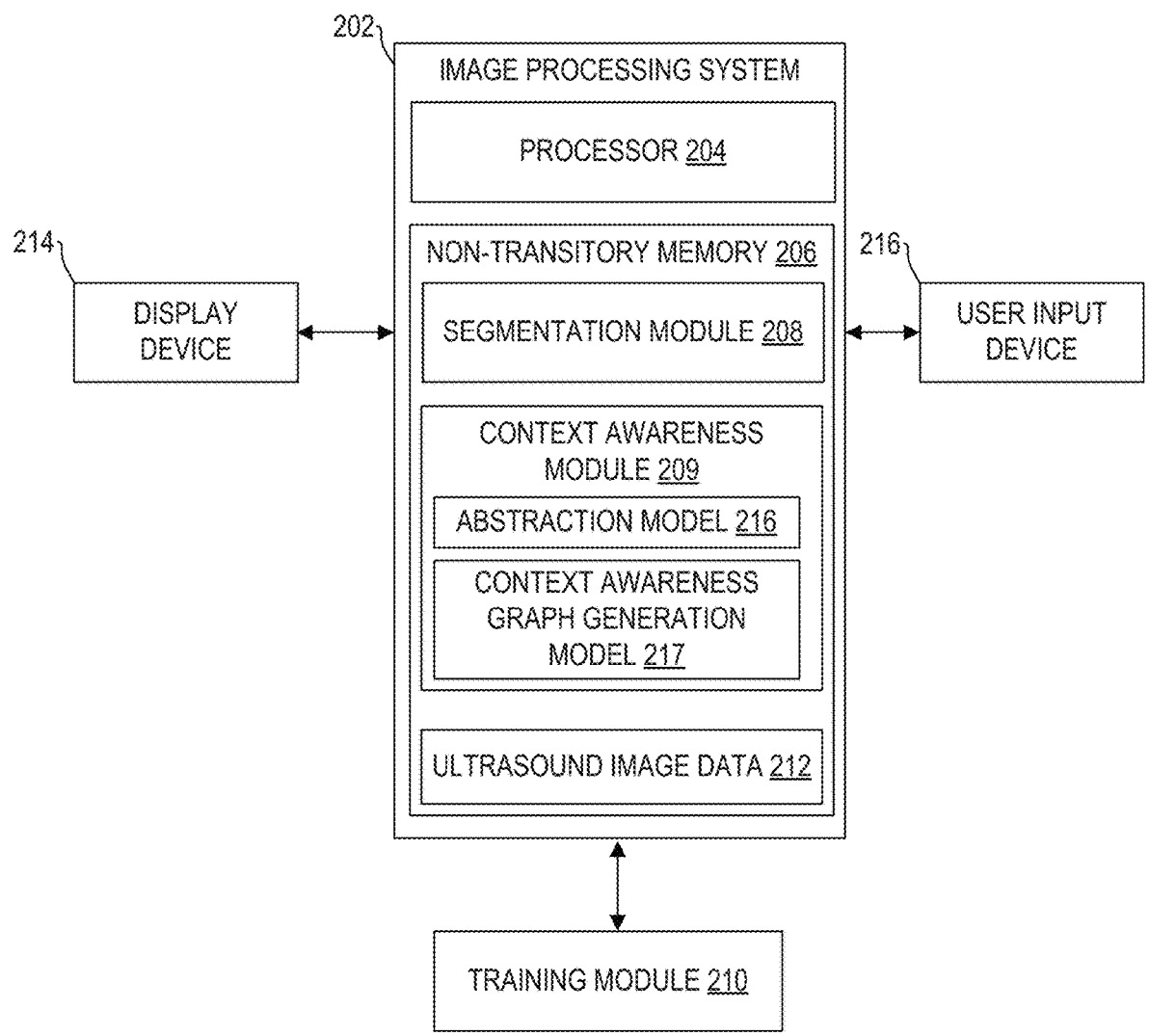
FIG. 2 is a schematic diagram illustrating a system for segmenting a scan image and generating a context awareness graph of the scan image, according to an exemplary embodiment.
Figure 4:
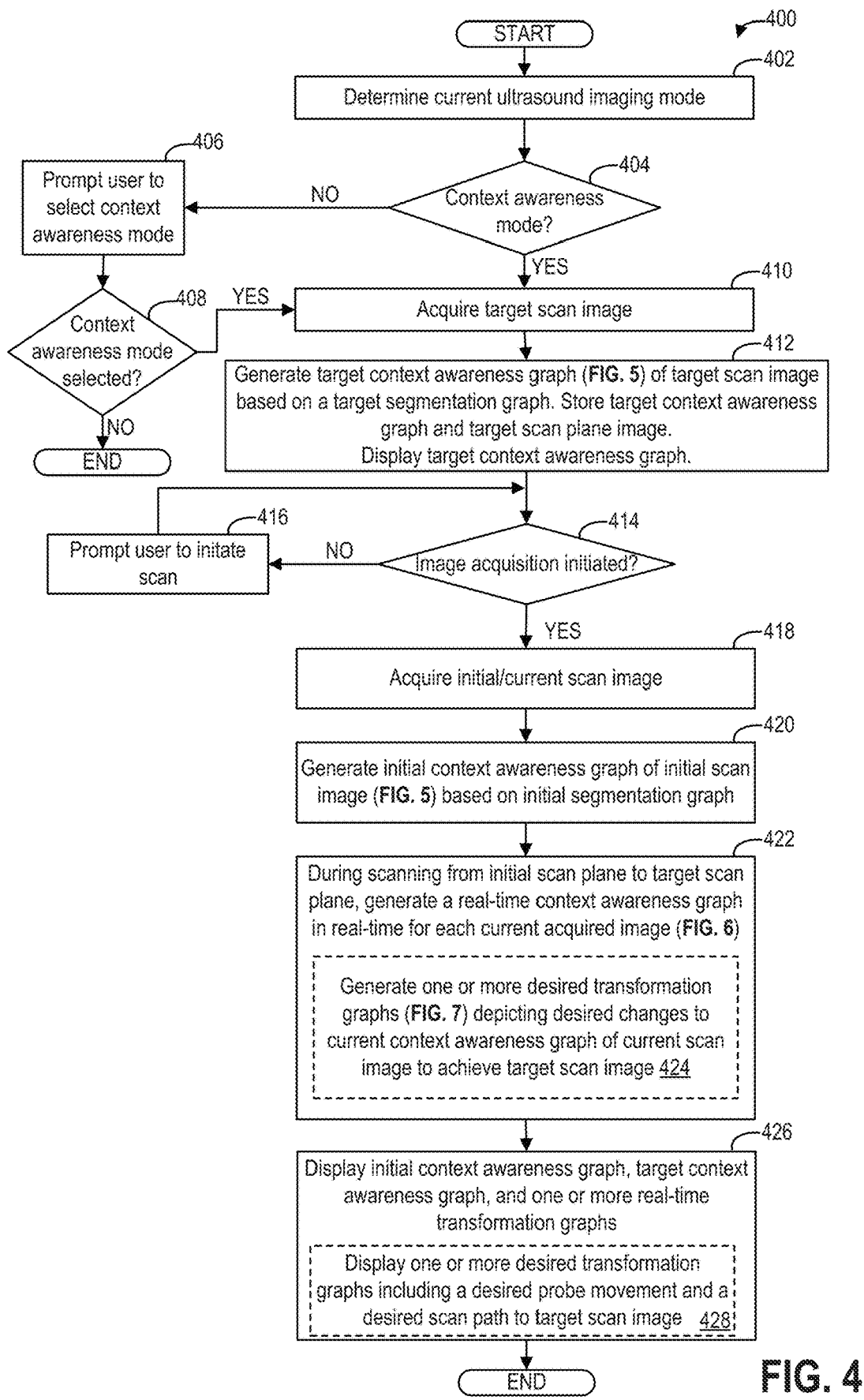
FIG. 4 shows a high-level flow chart illustrating a method for displaying a scan image according to an exemplary embodiment.
Figure 5:
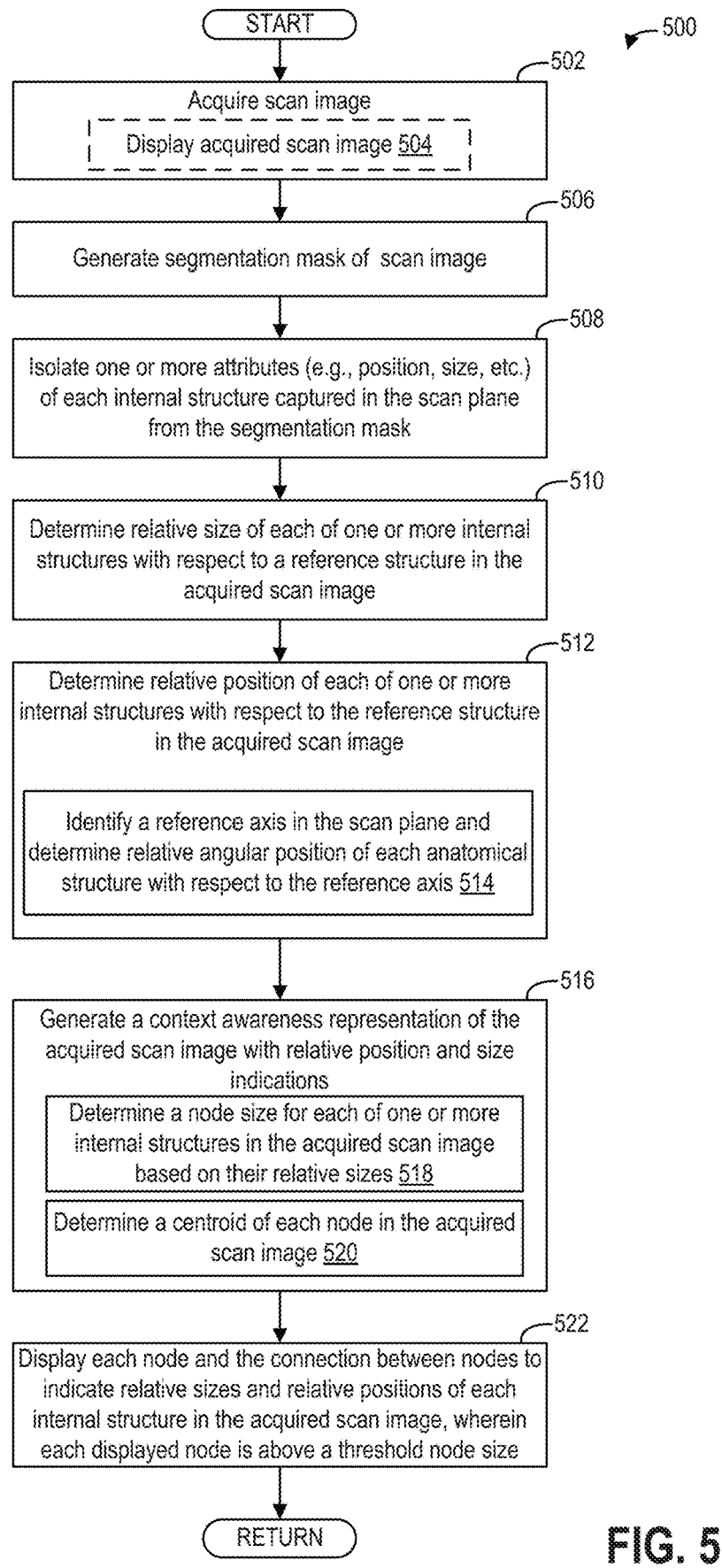
FIG. 5 shows a flow-chart illustrating a method for generating a context awareness graph for a scan image, according to an exemplary embodiment.
Figure 6:
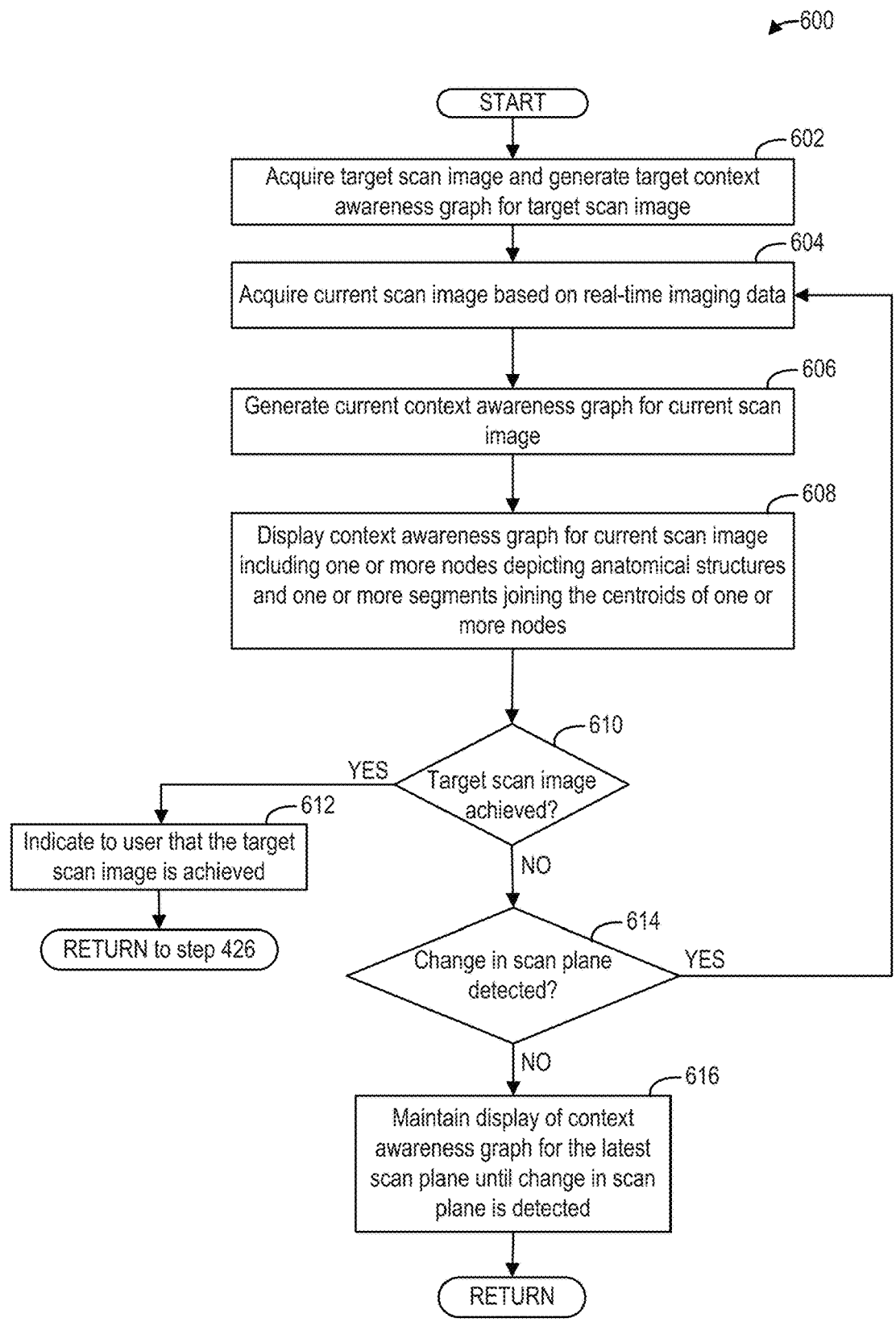
FIG. 6 shows a flow chart illustrating a method for generating a context awareness graph in real-time during ultrasound scanning, according to an exemplary embodiment.
Figure 7:
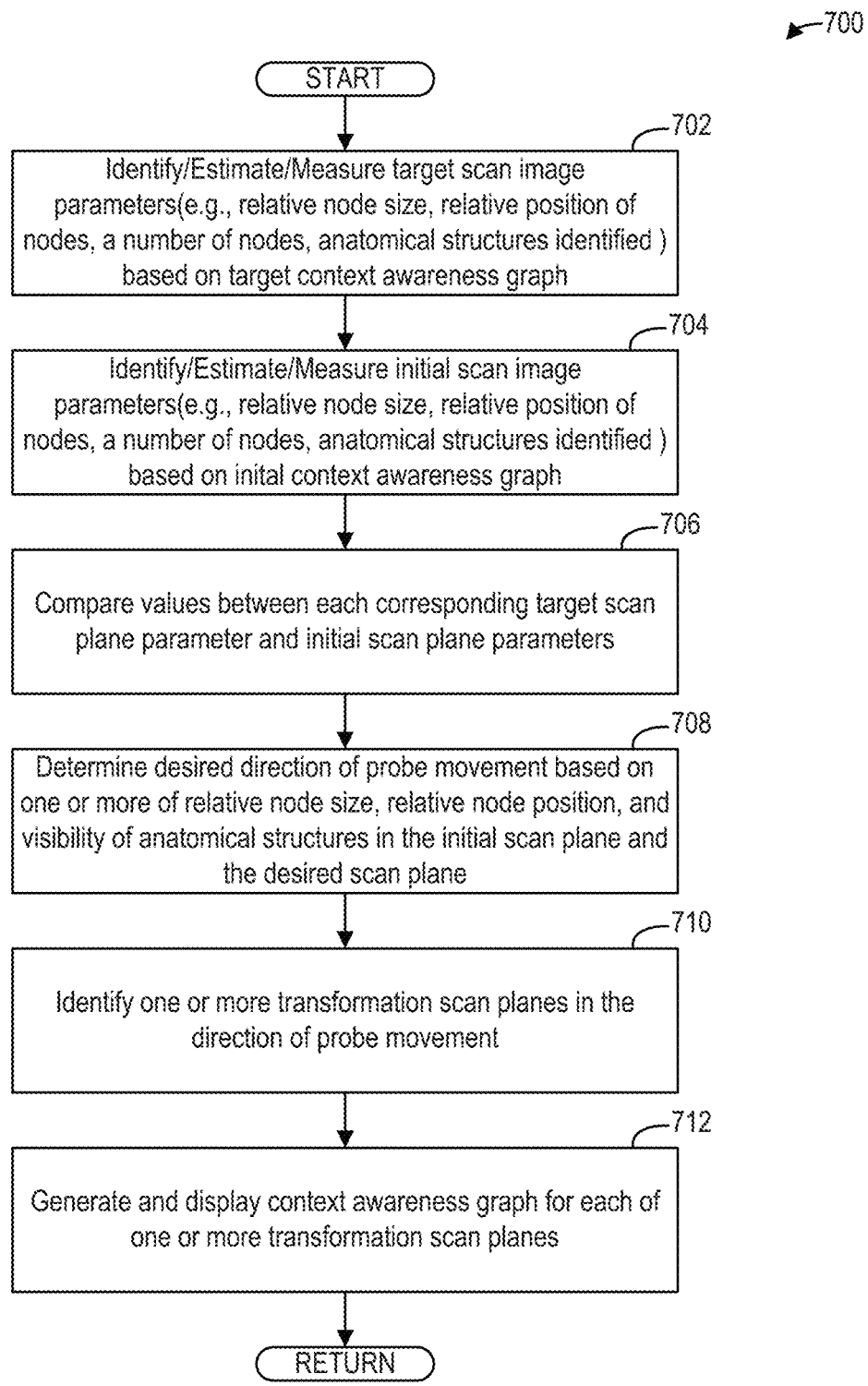
FIG. 7 shows a flow chart illustrating a method for generation of one or more desired transformation graphs to achieve a target scan plane during ultrasound scanning, according to an exemplary embodiment.
Figure 8A:
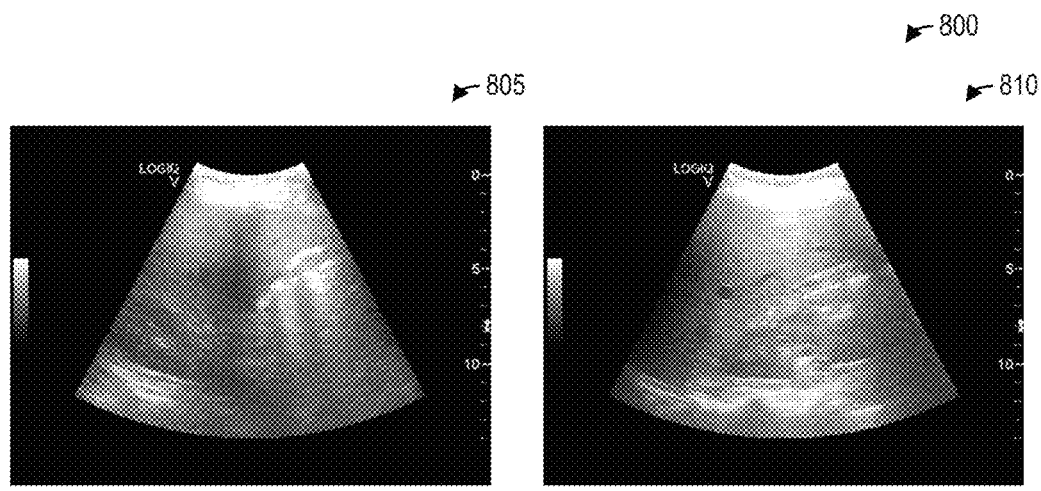
FIG. 8A shows an example set of two ultrasound scan images without internal features identified and without context awareness graphs represented.
Figure 8B:
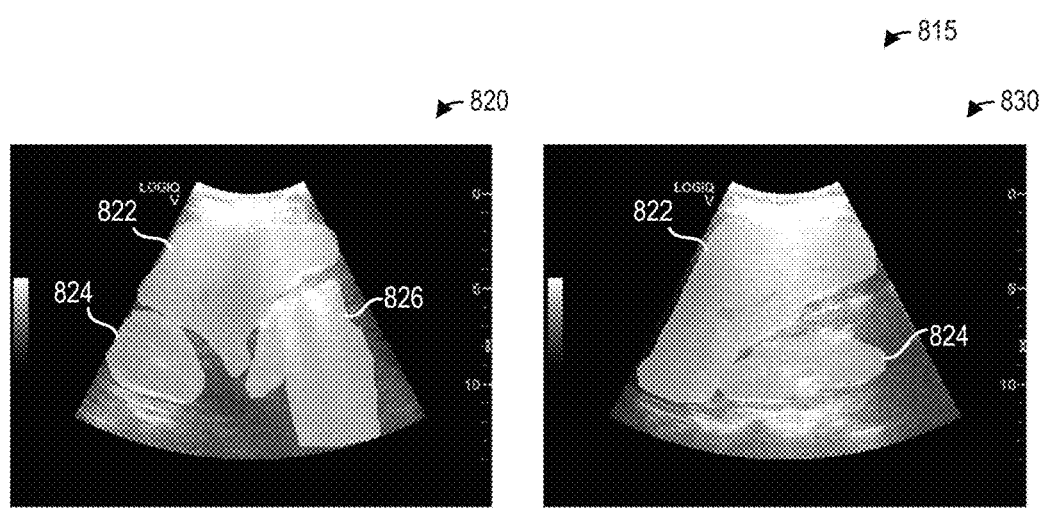
FIG. 8B shows the example set of ultrasound scan images of 8A with internal feature annotations and without context awareness graph.
Figure 8C:
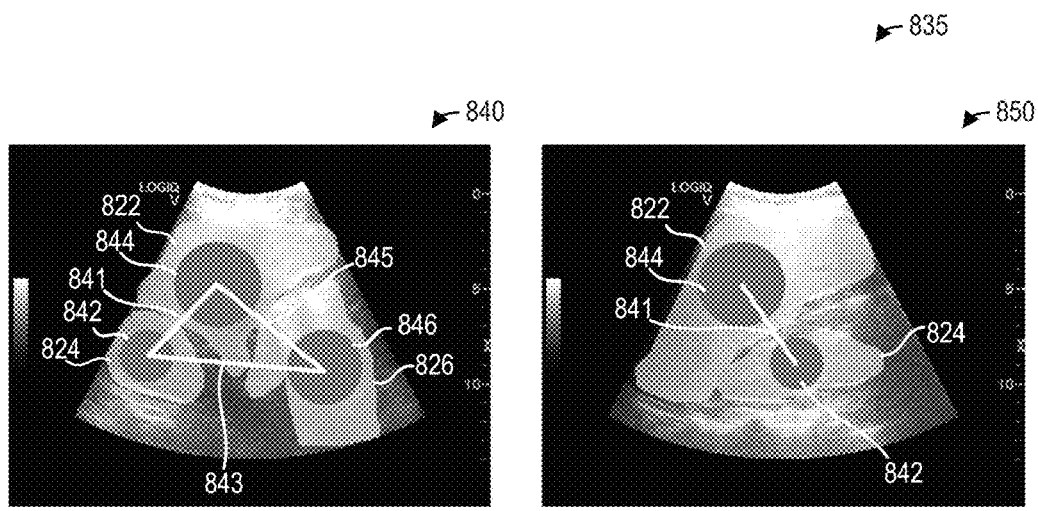
FIG. 8C shows the example set of ultrasound scan images of 8B including context awareness graphs.
Figure 9:
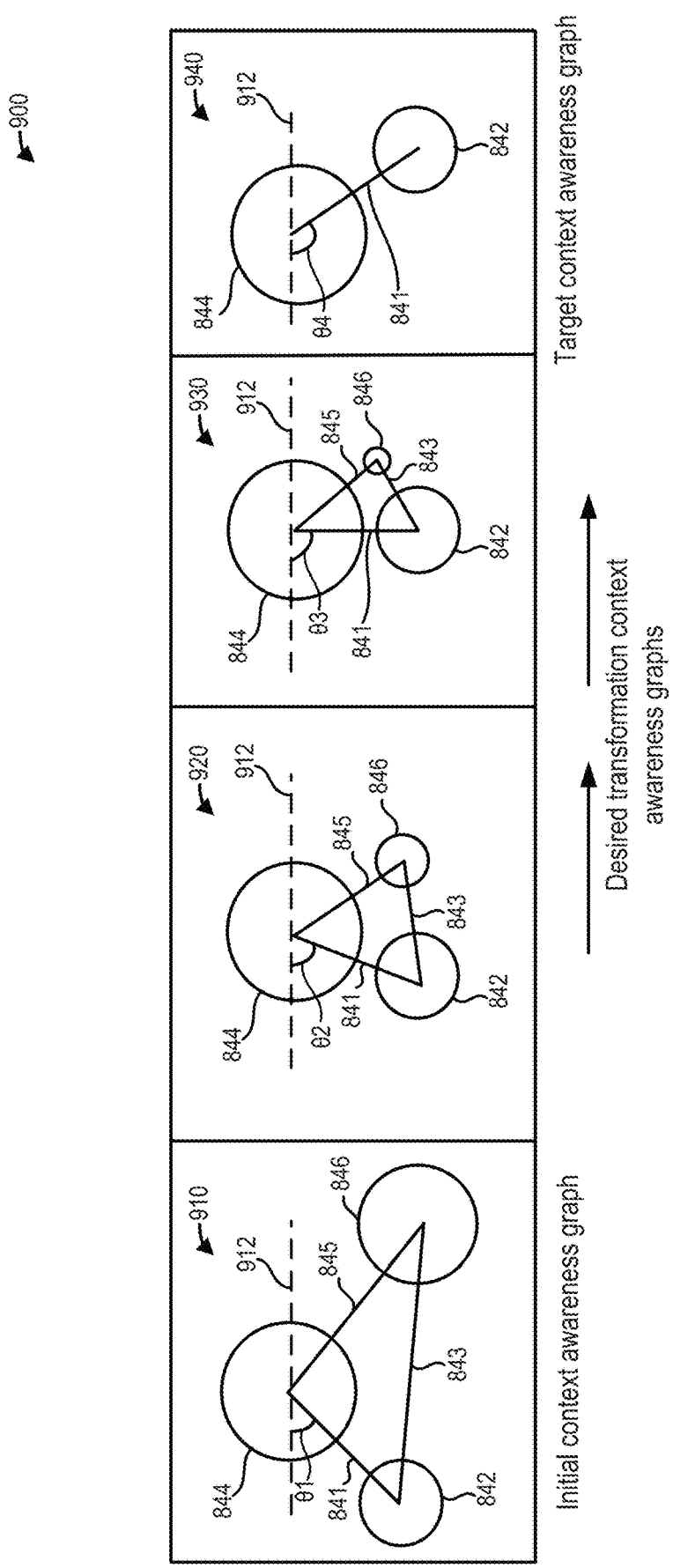
FIG. 9 shows example initial and target context awareness graphs for an initial scan image and a target scan image respectively, and one or more desired transformation graphs to obtain the target scan image, according to an exemplary embodiment.
Figure 10:
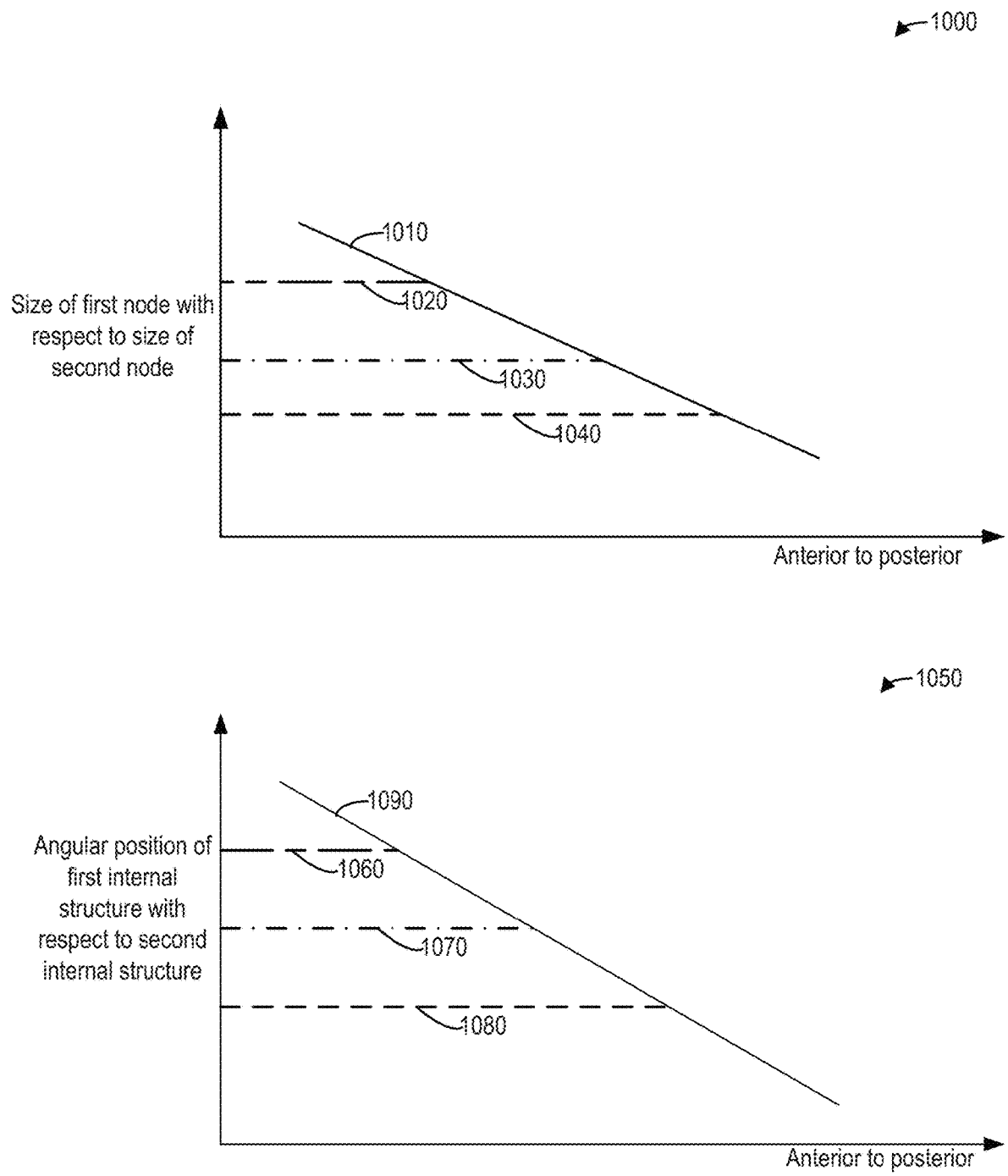
FIG. 10 shows example graphs illustrating visual change in size and positioning of an first internal feature with respect to an second internal feature and the corresponding correlation with scan direction during an ultrasound scan, according to an exemplary embodiment.
Figure 11:
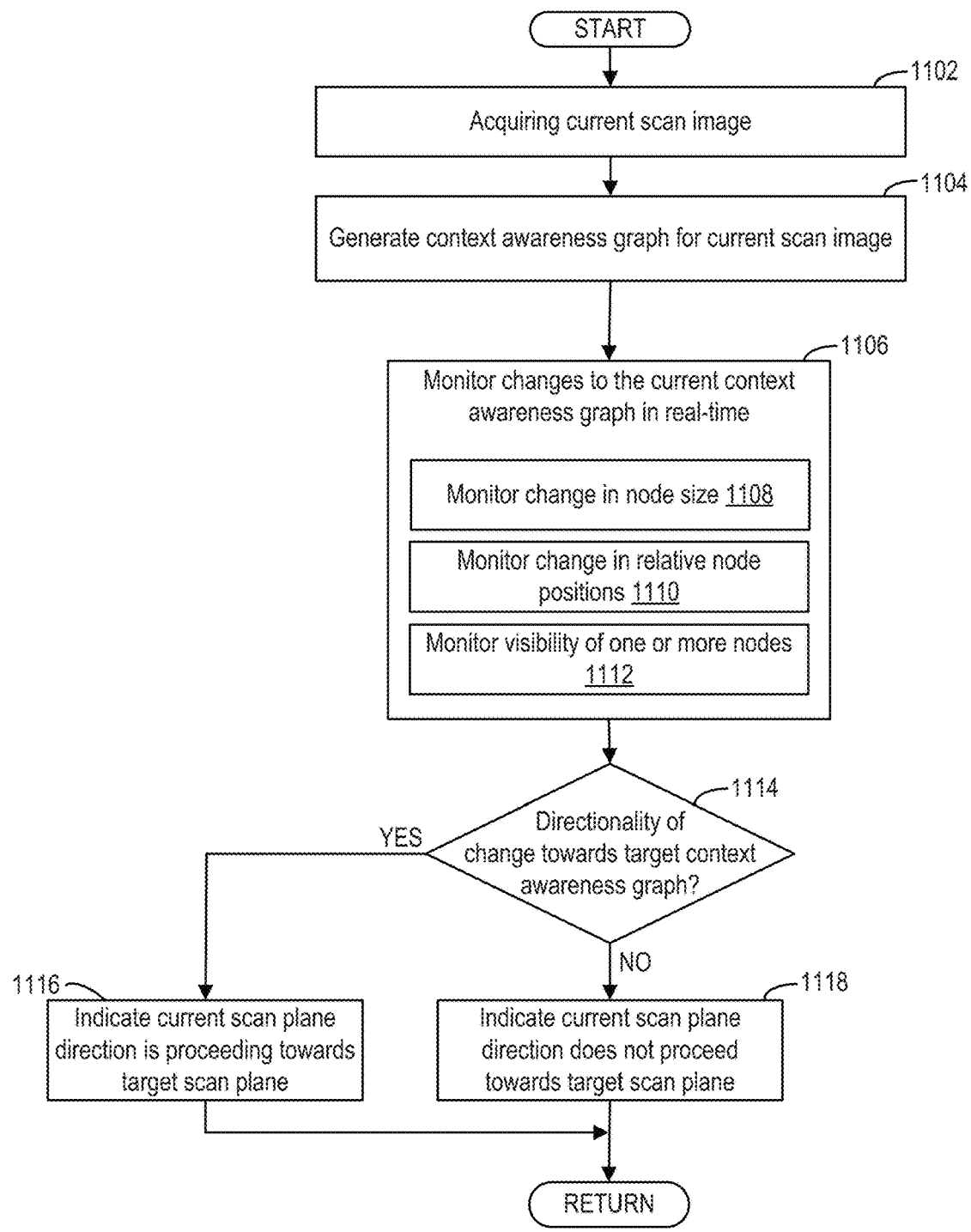
FIG. 11 shows a flow chart illustrating an example method for alerting a user regarding direction of probe movement during an ultrasound scan based on context awareness graphs of a current scan image and a target scan image, according to an exemplary embodiment.

An example ultrasound system including an ultrasound probe, a display device, and an imaging processing system are shown in FIG. 1. Via the ultrasound probe, ultrasound images may be acquired and displayed on the display device. The displayed images may be annotated with annotations that are generated using a segmentation model that may identify anatomical features in the ultrasound images. The segmentation model may be stored on and executed by the image processing system, as shown in FIG. 2. In some examples, the segmentation model may a convolution neural network (CNN), such as the CNN shown in FIG. 3. A context awareness graph for a scan image may be generated based on one or more attributes isolated from an output of the segmentation model. An example method for performing a medical scan, such as an ultrasound scan, in a context awareness mode is shown at FIG. 4, and an example method for generation of context awareness graph is shown in FIG. 5. The context awareness graph may be a pictorial representation of relative sizes and relative positions of one or more internal features visible in a scan image. Example initial and target scan images are shown at FIG. 8A. Example segmentation graphs of the initial scan image and the target scan image, including example annotations for one or more internal features, overlaid on respective initial and target scan images are shown at FIG. 8B. Example context awareness graphs generated based on relative position and relative size attributes of the internal features in the initial and target scan images are shown as overlays on corresponding displayed scan images at FIG. 8C. Further, example schematics of context awareness graphs (without underlying scan images) of the initial scan image, the target scan image, and one or more desired transformation graphs indicating desired changes to an initial context awareness graph of the initial scan image while moving the probe from an initial scan plane to a target scan plane are shown in FIG. 9. In one exemplary embodiment, context awareness graph of a scan image may be displayed in real-time based on real-time scan images displayed on a user interface of the ultrasound scanning system as shown at FIG. 6. In another exemplary embodiment, context awareness graph may be used to display a desired change in the scan image and/or the context awareness graph to arrive at the target scan plane as shown in FIG. 7. Additionally, based on the context awareness graphs of the current scan image and target scan image, the user may be guided in real-time towards moving in the desired direction towards a target scan plane to arrive at the target scan image, and alerted when moving away from the target scan plane as shown in FIG. 11. Thus, the location of a current scan plane and desired probe movement to target scan plane can be determined and displayed to the user based on the context awareness graphs of the initial and target scan images, which indicate changes in one or more of relative sizes of internal features and relative positioning of internal features. Example graphs illustrating correlation between relative sizes, relative location of one or more example anatomical features and direction of scan plane with respect to the greater human anatomy is shown at FIG. 10.

It may be appreciated that although the generation of context awareness graph is illustrated herein with respect to an ultrasound imaging system shown in FIG. 1, that the context awareness graph may be generated for any medical scan image, such as a MM scan image, CT scan image, SPECT image, X-ray image etc. For example, a medical scan image may be acquired by a processor of a medical imaging system. Upon acquiring the medical scan image, one or more internal features may be identified, via a segmentation artificial intelligence model, for example, and a corresponding segmentation output and/or graph may be generated. Using the segmentation output, one or more attributes of the medical scan image, including size and position attributes may be isolated, via a data abstraction protocol, for example. The isolated attributes may be used to determine relative sizes and relative positions for each internal feature identified in the medical scan image. The relative size and relative position information may be applied to a context awareness graph generation model to output a context generation graph for the medical scan image, where the context generation graph includes one or more nodes representing each internal feature and an overall shape of the context awareness graph, including nodes and one or more segments, representing relative positions of each internal feature.

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from features in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system.

A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processer 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. In some embodiments, the processor 116 may be configured as graphical processing unit with parallel processing capabilities. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical features and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat".

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 214 and a display device 216.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store segmentation module 208, context awareness module 209, and ultrasound image data 212. Segmentation module 208 may include one or more machine learning models, such as deep learning networks, comprising a plurality of weights and biases, activation functions, loss functions, gradient descent algorithms, and instructions for implementing the one or more deep neural networks to process input ultrasound images. For example, segmentation module 208 may store instructions for implementing a neural network, such as the convolutional neural network (CNN) 300, shown in FIG. 3. Segmentation module 208 may include trained and/or untrained neural networks and may further include training routines, or parameters (e.g., weights and biases), associated with one or more neural network models stored therein.

Image processing system 202 may be communicatively coupled to training module 210, which comprises instructions for training one or more of the machine learning models stored in segmentation module 208. Training module 210 may include instructions that, when executed by a processor, cause the processor to conduct one or more of the steps of method 600, discussed in more detail below. In one example, training module 210 includes instructions for receiving training data sets from ultrasound image data 212, which comprise sets of ultrasound images, associated ground truth labels/images, and associated model outputs for use in training one or more of the machine learning models stored in segmentation and tracking module 208. Training module 210 may receive ultrasound images, associated ground truth labels/images, and associated model outputs for use in training the one or more machine learning models from sources other than ultrasound image data 212, such as other image processing systems, the cloud, etc. In some embodiments, one or more aspects of training module 210 may include remotely-accessible networked storage devices configured in a cloud computing configuration. Non-transitory memory 206 may further store ultrasound image data 212, such as ultrasound images captured by the ultrasound imaging system of FIG. 1. For example, ultrasound image data 212 may store ultrasound images, ground truth output, iterations of machine learning model output, and other types of ultrasound image data. In some embodiments, ultrasound image data 212 may store ultrasound images and ground truth output in an ordered format, such that each ultrasound image is associated with one or more corresponding ground truth outputs.

In some examples, the outputs of segmentation module 208 are input to the context awareness module 209. The context awareness module 209 may implement an abstraction model 216 and a context awareness graph generation model 217, and output a context awareness graph. For example, the context awareness module 209 may store instructions for generating a context awareness graph for a scan image. The context awareness graph may comprise graphical marks such as geometrical shapes (e.g. circles, points, lines, boxes, and other geometric shapes) overlaid on ultrasound scan images to indicate relative positions and relative sizes of one or more internal features in the ultrasound scan image or in a region of interest on the ultrasound scan image. In this way, the context awareness graph may prescribe both relative size and relative orientations or relative positions of the one or more internal features with respect to each other and/or with respect to the greater anatomy to ensure that the user is able to identify a current scan plane and move the probe towards a target scan plane.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 216 may comprise one or more of a touchscreen, a keyboard, a mouse, a trackpad, a motion sensing camera, or other device configured to enable a user to interact with and manipulate data within image processing system 31. In one example, user input device 216 may enable a user to make a selection of an ultrasound image to use in training a machine learning model, or for further processing using a trained machine learning model.

Display device 214 may include one or more display devices utilizing virtually any type of technology. In some embodiments, display device 214 may comprise a computer monitor, and may display ultrasound images. Display device 214 may be combined with processor 204, non-transitory memory 206, and/or user input device 216 in a shared enclosure, or may be peripheral display devices and may comprise a monitor, touchscreen, projector, or other display device known in the art, which may enable a user to view ultrasound images produced by an ultrasound imaging system, and view segmentation annotations and context awareness graph annotations of the ultrasound scan images, and/or interact with various data stored in non-transitory memory 206.

It should be understood that image processing system 202 shown in FIG. 2 is for illustration, not for limitation. Another appropriate image processing system may include more, fewer, or different components.

Figure 3:
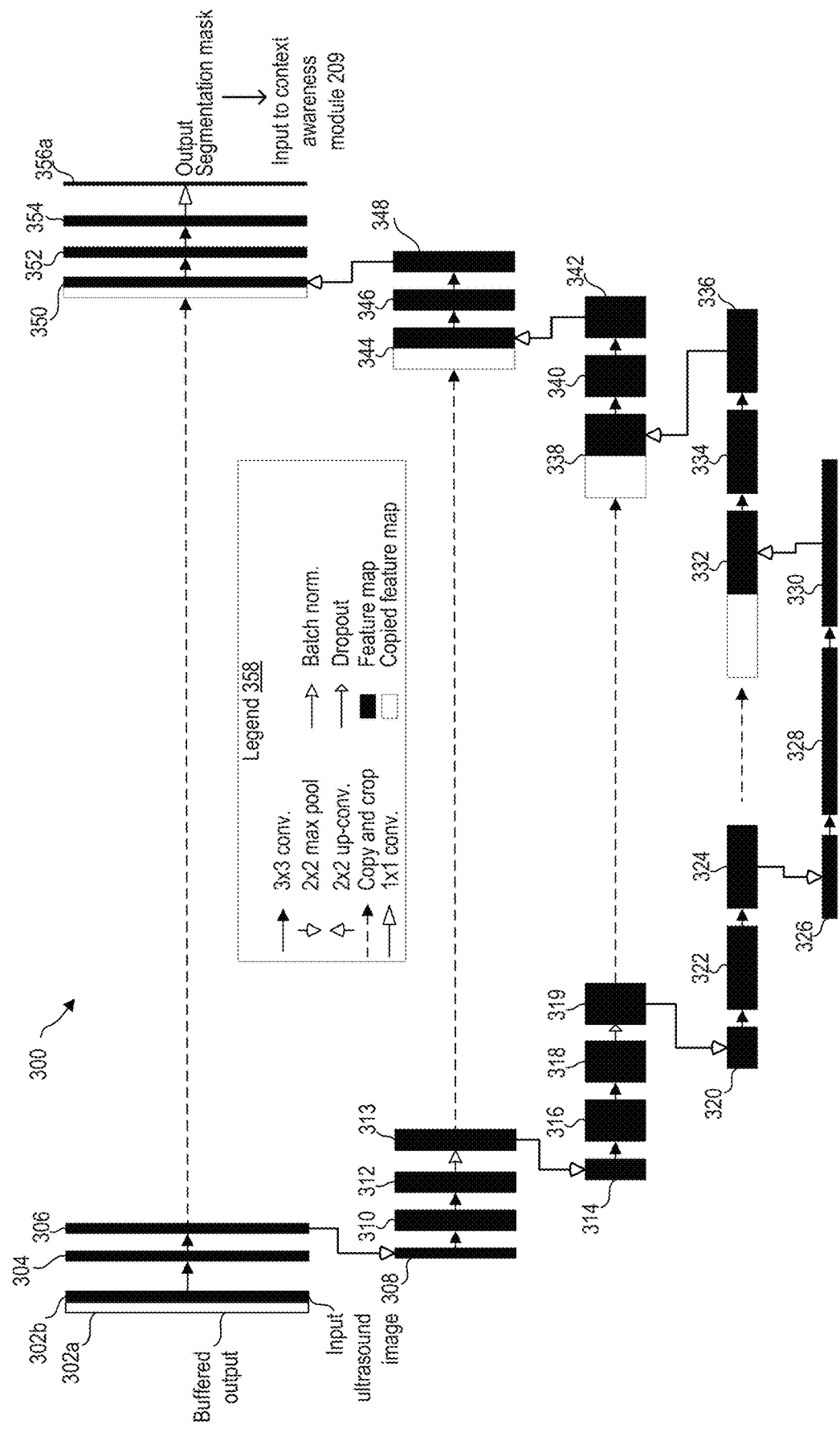
FIG. 3 is a schematic diagram illustrating a layout of an exemplary deep learning network which may be used to segment a scan image, and identify one or more internal features in the scan image, according to an exemplary embodiment.

Turning to FIG. 3, architecture for an example convolutional neural network (CNN) 300 is shown. CNN 300 represents one example of a machine learning model, which may be used to determine anatomy segmentation parameters, which then may be used to generate context awareness graphs for ultrasound scan images. CNN 300 comprises a U-net architecture, which may be divided into an autoencoder portion (descending portion, elements 302b-330) and an autodecoder portion (ascending portion, elements 332-356a). CNN 300 is configured to receive ultrasound images comprising a plurality of pixels/voxels, and map the input ultrasound scan image to generate anatomical segmentation of the scan image. CNN 300 includes a series of mappings, from an input image tile 302b which may be received by an input layer, through a plurality of feature maps, and finally to an output layer 356a.

The various elements comprising CNN 300 are labeled in legend 358. As indicated by legend 358, CNN 300 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 358. Rightward pointing solid black arrows indicate 3×3 convolutions with stride of one, wherein output from a 3×3 grid of feature channels of an immediately preceding feature map are mapped to a single feature channel of a current feature map. Each 3×3 convolution may be followed by an activation function, wherein, in one embodiment, the activation function comprises a rectified linear unit (ReLU).

Downward pointing hollow arrows indicate 2×2 max pooling, wherein the max value from a 2×2 grid of feature channels is propagated from an immediately preceding feature map to a single feature channel of a current feature map, thereby resulting in a 4-fold reduction in spatial resolution of the immediately preceding feature map.

Upward pointing hollow arrows indicate 2×2 up-convolutions, which comprise mapping output from a single feature channel of an immediately preceding feature map to a 2×2 grid of feature channels in a current feature map, thereby increasing the spatial resolution of the immediately preceding feature map 4-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with arcuate hollow heads indicate batch normalization operations, wherein a distribution of activations of an input feature map are normalized. Rightward pointing arrows with a short hollow triangular head indicates a dropout operation, wherein random or pseudo-random dropout of input neurons (as well as their inputs and outputs) occurs during training.

In addition to the operations indicated by the arrows within legend 358, CNN 300 includes feature maps that are represented in FIG. 3 by solid filled rectangles, wherein feature maps comprise a height (top to bottom length as shown in FIG. 3, which corresponds to a y spatial dimension in an x-y plane), width (not shown in FIG. 3, assumed equal in magnitude to height, and corresponds to an x spatial dimension in an x-y plane), and depth (a left-right length as shown in FIG. 3, which corresponds to the number of features within each feature channel). Likewise, CNN 300 includes copied and cropped feature maps that are represented in FIG. 3 by hollow (unfilled) rectangles, wherein copied feature maps comprise height (top to bottom length as shown in FIG. 3, which corresponds to a y spatial dimension in an x-y plane), width (not shown in FIG. 3, assumed equal in magnitude to height, and corresponds to an x spatial dimension in an x-y plane), and depth (a length from a left side to a right side as shown in FIG. 3, which corresponds to the number of features within each feature channel).

Starting at input image tile 302*b* (herein also referred to as an input layer), data corresponding to an ultrasound image may be input and mapped to a first set of features. In some embodiments, the input data is pre-processed (e.g., normalized) before being processed by the neural network. The weights/parameters of each layer of CNN 300 may be learned during a training process, wherein matched pairs of input and expected output (ground truth output) are fed to CNN 300. Parameters may be adjusted based on a gradient descent algorithm, or other algorithm, until the output of CNN 300 matches the expected output (the ground truth output) within a threshold degree of accuracy.

As indicated by the solid black rightward pointing arrow immediately to the right of input image tile 302*b*, a 3×3 convolution of the feature channels of input image tile 302*b* is performed to produce feature map 304. As discussed above, a 3×3 convolution includes mapping input from a 3×3 grid of feature channels to a single feature channel of a current feature map, using learned weights, wherein the learned weights are referred to as a convolution filter. Each 3×3 convolution in CNN architecture 300 may include a subsequent activation function, which in one embodiment includes passing the output of each 3×3 convolution through a ReLU. In some embodiments, activation functions other than ReLUs may be employed, such as Softplus (also referred to as SmoothReLUs), leaky ReLUs, noisy ReLUs, exponential linear units (ELUs), Tanh, Gaussian, Sinc, Bent identity, logistic functions, and other activation functions known in the art of machine learning.

Output layer 356*a* may comprise an output layer of neurons, wherein each neuron may correspond to a pixel of a segmented ultrasound image, and wherein output of each neuron may correspond to a predicted anatomical feature (or lack of the anatomical feature) in a given location within the input ultrasound scan image. For example, the output of a neuron may indicate whether the corresponding pixel of segmented ultrasound image is part of a vessel, a nerve, a bone, an artery, etc., or part of an unidentified feature. Thus, output layer 356*a* may include segmentation information of the input ultrasound scan image, where the segmentation information includes identification, relative positions, and relative sizes of one or more internal anatomical features in the ultrasound scan image.

The output layer 356*a* may be input into context awareness module, such as context awareness module 209 at FIG. 2. The context awareness module may include instructions to receive the output layer 356*a* from the segmentation module, and abstract segmentation information, including anatomical feature identification information, position information for each identified anatomical feature, and size information for each identified anatomical feature in the input ultrasound scan image. The position information includes relative position information for each identified anatomical feature with respect to every other anatomical feature identified in the scan image and with respect to the greater human anatomy. The size information includes relative size information, based on visibility in the scan image, for each identified anatomical feature with respect to every other anatomical feature identified in the scan image. The size information may further include relative size information with respect to the greater human anatomy.

The segmentation of relative size and relative position information for the anatomical features in the ultrasound scan image may take into account lateral, axial, and temporal resolution of the ultrasound scan image. The segmentation information including anatomical feature identification data, relative position data, and relative size data that are abstracted out from the output layer may then be used to generate a context awareness graph depicting a context awareness relationship showing relative sizes and relative positions of the anatomical features visible in the scan image.

In one exemplary embodiment, the context awareness graph may be generated in real-time for each scan image and displayed as an overlay with the corresponding scan image. In another exemplary embodiment, additionally, desired context awareness graph showing the desired changes to the current context awareness graph as the user moves from the current scan plane to the target scan plane may be generated and displayed to the user. In this way, a context awareness graph may be generated in real-time for an ultrasound scan image, and may depict relative size and relative position information in addition to identification information for each anatomical feature visible in the ultrasound scan image. The real-time relative size and relative position information may be used to guide a user from a current scan plane to a target scan plane during an ultrasound exam. As a result, reliance on sensor-based feedback systems, such as haptic feedback, is reduced, and the user may be visually guided towards the target scan plane. Furthermore, the context awareness graph allows a user to determine if the scan is progressing in the desired direction, and as such, reduces the time to arrive at the target scan plane and improves an overall efficiency of the ultrasound evaluation process.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 3, or may replace one or more of the shown layers/feature maps.

It should be understood that the architecture and configuration of CNN 300 shown in FIG. 3 is for illustration, not for limitation. Any appropriate neural network can be used, such as ResNet, recurrent neural networks, General Regression Neural Network (GRNN), etc. One or more specific embodiments of the present disclosure are described above in order to provide a thorough understanding. The skilled artisan will understand that specific details described in the embodiments can be modified when being placed into practice without deviating the spirit of the present disclosure.

Turning to FIG. 4, a high-level flow chart illustrating an example method 400 for performing an ultrasound scan in a context awareness mode is shown. Method 400 is described with regard to the systems and components of FIGS. 1, 2, and 3, although it should be appreciated that method 400 may be implemented with other systems and components without departing from the scope of the present disclosure. For example, method 400 may be stored as executable instructions in non-transitory memory, such as memory 120, and may be executed by a processor, such as processor 116, of the ultrasound imaging system 100, or may be implemented by one or more of the above disclosed systems, such as image processing system 202. Method 400 may be initiated by a medical personnel, such as a physician, or an operator, such as sonographers.

Method 400 begins at 402. At 402, method 400 includes determining a current ultrasound imaging mode. The current ultrasound imaging mode may be determined according to user input received at a user interface of the ultrasound system, such as user interface 115 of FIG. 1. An operator of the ultrasound system may select an imaging mode and/or protocol via the user interface, or otherwise enter input indicating a desired ultrasound imaging mode and/or desired imaging protocol. Example ultrasound imaging modes may include B-mode imaging, Doppler imaging, M-mode imaging, and the like.

Further, the ultrasound imaging mode indicated by the operator may include a context awareness mode, during which a scan image is processed to generate and display a context awareness graph to the user, as detailed further below. In some examples, the selection of imaging mode may be optional, and the scan image may be displayed along with the context awareness graph even without the user selection. Other imaging modes, such as segmentation display mode, where a segmentation graph identifying and depicting one or more anatomical features visible in the scan image, are also within the scope of the disclosure.

Further, example ultrasound imaging protocols may include cardiac imaging protocols (e.g., echocardiograms), abdomen imaging, fetal imaging, renal imaging, and/or other anatomy-specific protocols. Additionally, some example ultrasound imaging protocols may be based on a type of procedure being performed along with or during the imaging, such as a resuscitation protocol, needle biopsy protocol, etc. The imaging mode and/or protocol may dictate which type of ultrasound probe is used, how the ultrasound probe is controlled during the imaging session (e.g., signal frequency, gain, beam focus, etc.), how the acquired image information is processed, and/or what types of images the operator is to acquire during the imaging session, which may include how the operator is to position and control the ultrasound probe during the imaging session. In some examples, additionally, the user may indicate a desired exam type. For example, a list of possible exam types may be displayed, including internal organs, muscle tissues, vessels, tendons, etc. and the operator may click on the desired exam type, instructing the processor to load settings suitable for the type of exam.

Continuing on to 404, method 400 includes confirming if the context awareness mode has been selected. If YES, method 400 proceeds to 410 to operate the ultrasound scan in the context awareness mode. If the context awareness mode is not selected, method 400 may include, at 406, prompting the user to select the context awareness mode, and further, at 408, confirming the selection of the context awareness mode. If the context awareness mode is selected after prompting at 408, method 400 proceeds to 410. Otherwise, method 400 may end.

At 410, method 400 includes acquiring a target scan image. In one example, the target scan image may be acquired based on user selection and/or input. For example, the user may enter one or more of a desired body plane (e.g. transverse, longitudinal, or coronal), a desired internal body area (e.g., upper or lower abdomen, right or left subcostal, etc.), one or more desired anatomical features to be imaged, and a medical condition (e.g., gall bladder stone etc.) to be evaluated. Additionally, the user input regarding the imaging protocol, as discussed at 402, may be used in selecting the target scan image. Based on the user input, a plurality of predetermined target scan images may be displayed to the user for user selection. In this way, the target scan image may be acquired based on user selection from a plurality of predetermined scan images stored in non-transitory memory. In another example, the target scan image may be acquired based on a selected region of interest within a predetermined desired scan image.

Upon acquiring the target scan plane, method 400 may include, at 412, generating a context awareness graph for the target scan plane (also referred to herein as target context awareness graph). Details of generating a context awareness graph will be described with respect to FIG. 5. Briefly, the target context awareness graph may be generated based on a segmentation graph of the target scan image (also referred to herein as the target segmentation graph). A segmentation graph may identify one or more features visible in a scan image of the target scan plane. Upon generating the context awareness graph of the target scan image based on the segmentation graph, the processor may store the context awareness graph of the target scan image, the segmentation graph of the target scan image, and the target scan image in the non-transitory memory.

Further, upon generating the context awareness graph for the target scan image, method 400 may include displaying the context awareness graph of the target scan plane to the user. In one example, the context awareness graph may be displayed as an overlay on the target scan image on the user interface, such as a display device 118 of the ultrasound system 110. In another example, the context awareness graph may be displayed adjacent to the target scan image.

Continuing on to 414, method 400 includes determining if the user has initiated image acquisition of a subject. Initiation of image acquisition may be determined based on one or more of a signal received from an ultrasound probe, such as probe 106 of FIG. 1. If the image acquisition has not commenced, method 400 includes, at 416, prompting the user to start imaging. If the image acquisition is initiated, method 400 includes, at 418, acquiring an initial scan image based on ultrasound scan data received from the ultrasound probe.

Next, at 420, method 400 includes generating a context awareness graph for the initial scan image (also referred to herein as the initial context awareness graph) based on the initial ultrasound scan image (hereinafter initial scan image). Details of generating the context awareness graph will be described below with respect to FIG. 5. Briefly, the context awareness graph of the initial scan plane may provide an indication of the relative positions and sizes of the internal features visible in initial scan image. The context awareness graph of the initial scan image may be generated based on a segmentation graph of the initial scan image. The segmentation graph may provide an indication of identification of the internal features visible in the initial scan image of the initial scan plane. The segmentation graph may be generated based on a segmentation model using an artificial intelligence protocol, as discussed above with respect to FIGS. 2 and 3.

Upon generating the initial context awareness graph, method 400 proceeds to 422. At 422, method 400 includes during scanning from initial scan plane to target scan plane, generating a real-time context awareness graph in real-time for each acquired image. Details of generating context awareness graphs in real-time will be elaborated with respect to FIG. 6. Briefly, as the user moves the probe towards the target scan plane from the initial scan plane, for each scan image generated and displayed on the user interface, a corresponding context awareness graph may be generated and displayed. As the user navigates the probe to go to the target scan plane, the user may visualize the changes to the scan image through the context awareness graph, and determine if the shape of the context awareness graph is proceeding towards the context awareness graph of the target scan plane, and adjust the probe position accordingly. In this way, context awareness graphs may be utilized to guide the user towards the target scan plane based on the scan images. As such, the need to implement sensors and additional electronics for tracking probe movement and guiding the user is also reduced.

Additionally or alternatively to generating context awareness graph in real-time, method 400 includes, at 424, generating one or more desired transformation graphs that depict the desired changes to the context awareness graph of the initial scan image to achieve the target context awareness graph. The generation of one or more desired transformation graphs will be described with respect to FIG. 7 below. Briefly, one or more desired transformation graphs provide a graphical annotation of how the initial context awareness graph is expected to change when progressing in the desired direction from the initial scan plane to the target scan plane.

Thus, the user may use the one or more transformation graphs to determine if the user is moving the probe towards the target scan plane. As a result, the user may arrive at the target scan plane via a more efficient path. Consequently, time taken to perform the medical scan and further, efficiency and quality of the scan is also improved as the context awareness graph also enables the user to identify when the probe is at the target scan plane. Thus, image quality is also improved.

Next, method 400 proceed to 426. At 426, method 400 includes displaying initial context awareness graph, target context awareness graph, and one or more real time context awareness graphs as the ultrasound scan proceeds from the initial scan plane to the target scan plane. Additionally or alternatively, as indicated at 426, one or more desired transformation graphs including a desired probe movement and a desired scan path with respect to the greater human anatomy to the target scan plane may also be displayed. As discussed above, the context awareness graph may be displayed as an overlay on the target scan image, or adjacent to the target scan image on the user interface, such as a display device 118 of the ultrasound system 110. The type of display, overlay versus side-by-side/adjacent may be based on user selection and/or input.

In this way, the ultrasound system may be operated in a context awareness mode based on a target context awareness graph, an initial context awareness graph, real-time context awareness graph as the user performs the medical scan and moves the probe from the initial scan plane to the target scan plane.

Thus, the context awareness graph helps the user to locate the scan plan in a human anatomy. Further, it can also serve to guide the user reach a desired scan plan which can be represented as the desired context awareness graph.

Turning to FIG. 5, a flow chart illustrating an example method 500 for generating a context awareness graph for a scan image is shown. As discussed herein, context awareness graph may include a representation of relative sizes and relative positions of one or more internal features, which includes anatomical features visible in a scan image produced from medical imaging scan, such as an ultrasound scan. The context awareness graph provides context information of one or more of internal features visible in the scan image relative to each other and relative to greater human anatomy. The scan image may be obtained by image processing based on information received from the ultrasound probe at a scan plane. Method 500 may be implemented by one or more of the above disclosed systems, such as image processing system 202 and/or ultrasound system 100, though it should be appreciated that method 500 may be implemented with other systems and components without departing from the scope of the present disclosure.

Method 500 begins at 502. At 502, method 500 includes acquiring a scan image. The acquired scan image may include one or more of a current scan image based on signals received from an ultrasound transducer and a target scan image based on a selection of the target scan image by the user from a selection of predetermined target scan images stored in non-transitory memory. For example, acquiring a scan image may include acquiring image information of a patient using an ultrasound transducer. The ultrasound transducer transmits ultrasonic signals while scanning the patient and receives reflected signals. The acquired data may be processed into a scan image by the processor. In another example, while operating the ultrasound system in a context awareness mode, an operator may select a target scan image from a selection of predetermined target scan images stored in non-transitory memory.

Optionally, at 504, method 500 includes displaying the scan image, without one or more of segmentation graph and context awareness graph. For example, the acquired ultrasound images may be displayed without indications of identified anatomical features, relative positions and relative sizes of the identified anatomical features, such as the ultrasound images shown at 805 and 810 of FIG. 8A, and further described below.

Upon acquiring the scan image, method 500 includes at 506 generating a segmentation mask (also referred to as segmentation output) of the scan image. Generating the segmentation mask may include entering the acquired scan image as an input to a segmentation model. In some examples, the segmentation model is a CNN, having an autoencoder-autodecoder type architecture, such as CNN 300 shown in FIG. 3. It will be appreciated that other artificial intelligence models for learning the internal features in an ultrasound scan image may be implemented and are within the scope of the disclosure. The segmentation model may generate, as a first output, a segmentation mask of the acquired scan image. Thus, the segmentation mask is an output of the segmentation model, and may include an identity of one or more internal features present in the acquired scan image. A segmentation graph may be generated from the segmentation mask and may include an estimated outline and/or highlight of one or more internal features in the acquired scan image. Example segmentation graphs interposed on the scan images are shown at 820 and 830 of FIG. 8B, and further described below.

Next, upon generating the segmentation mask, at 508, method 500 includes isolating one or more attributes including size, position, and density of one or more internal features visible in the scan plane. In some examples, other additional attributes such as axial and lateral resolution that may be utilized for generating a context awareness graph, may be isolated. Isolating one or more attributes from the segmentation mask may include entering the segmentation output of the segmentation model, as a second input, to the context awareness module. The context awareness module may implement an abstraction model, such as abstraction model 216 at FIG. 2, which may be directed or non-directed, cyclic or acyclic graphs to extract one or more attributes from the segmentation mask including size, position, density, resolution, and identification, of each internal feature captured in the acquired scan image.

Continuing on to 510, method 500 includes determining a relative size of each internal feature in the acquired scan image. Specifically, the relative size of each internal feature is with respect to the other internal features in the acquired scan image. In an exemplary embodiment, determining the relative size of each internal feature may include normalizing a size of each internal feature with respect to a reference feature in the acquired scan image. Normalizing the size may include calculating one or more of an area and volume of each internal feature with respect to a reference feature in the acquired scan image. As an example, a size of each internal feature may be an area defined by a boundary of the respective internal feature, and a relative size may be based on the area of the internal feature and an area of the reference feature. In other examples, the size may be a volume occupied by the internal feature in the acquired scan image, and the relative size may be based on the volume of the internal feature with respect to a volume of the internal feature. Further, the determination of the size of the internal feature may take into account a resolution, such as a spatial resolution including a lateral resolution and an axial resolution, of the acquired scan image.

As an illustrating example, an acquired scan image may capture a liver, a kidney, and a portion of large intestine/bowel. In the above example, the kidney may be selected as the reference feature, and relative sizes (normalized area and/or volume) of the liver and the portion of the large intestine/bowel may be determined.

It may be noted that the reference feature may be present in the acquired scan image, and thus, the selection of reference feature may change based on the acquired scan image which is dependent on the portion of anatomy under examination.

Furthermore, in some examples, when a target scan image is selected and a current scan image is being processed to generate a current context awareness graph, the selected reference feature may be present in the current scan image as well as the target scan image. In other words, the reference feature may be imaged at both the initial and the target scan planes. In yet another example, if the current scan image does not include any internal feature that is also present in the target scan image, any internal feature in the current image may be used as the reference feature.

Next, at 512, method 500 includes determining a relative position of each internal feature in the acquired scan image relative to the reference feature. As discussed above, the reference feature may be an internal feature that is visible in the acquired scan image. In some embodiments, determining the relative positions of the internal features may include determining x and y coordinates of a selected point for each internal feature, where the x coordinate is with respect to an axial axis perpendicular to the direction of propagation of the ultrasonic waves, and the y coordinate is with respect to a lateral axis along the direction of propagation of the ultrasonic waves. The selected point may be a centroid of the internal feature or the most internal point, for example. Relative positions can be fine (connected graph of centroids) or coarse grain descriptors (above/below, right/left).

Further, the relative position may include a relative distance between the one or more internal structures. For example, a distance between two internal features may be indicated by a length of the segment joining the two nodes corresponding to the two internal features.

In further embodiments, as indicated at 514, determining relative positions of one or more anatomical features may include identifying a reference axis in the scan image and determining an angular position for each anatomical feature with respect to the reference axis. For example, in a scan image including a first, a second, and a third internal feature, a reference axis may pass through a first centroid of a first internal feature in a scan image in a transverse direction, for example. An angle at which a second centroid of a second internal feature in the scan image is positioned with respect to the reference axis may be determined. Similarly, if the scan image shows a third internal feature, a second angle at which a third centroid of the third internal feature is positioned with respect to the reference axis may be determined. The relative position information, including the relative angular positions may be used to track a progress of an ultrasound evaluation process. For example, the relative position information may be used to determine if an ultrasound scan is progressing from a current scan image towards a target scan image, as discussed further with respect to FIG. 11.

Continuing on at 516, method 500 includes generating a context awareness representation (herein referred to alternatively as context awareness graph) of the acquired scan image, including relative size and relative position indications. Generating the context awareness representation of the acquired scan image may include entering the abstracted and normalized attributes, including relative size and relative position attributes (from 510 and 512 respectively), as inputs to a context awareness graph generation model, such as the context awareness graph generation model 217 at FIG. 2.

Generating the context awareness representation includes, at 518, determining a node size for each internal feature based on the relative size of the respective internal feature. That is, the relative size of the respective internal feature with respect to other internal features in the scan image. For example, for a scan image including an internal feature and one or more other internal features, the internal feature may be represented by a node in the context awareness graph. The node may be any geometrical shape (e.g., circular, oval, square, or any other geometric shape) and may provide a graphical representation of the internal feature visible in the scan image, where the node size is based on a relative size of the internal feature with respect to the one or more other internal features visible in the scan image (e.g., reference feature as discussed at 510). Further, the node size may be adjusted based on changes to the relative size of the internal structure. Specifically, during a scan, if the relative size of the internal structure in the scan image increases with respect to the one or more other internal features, the node size in the context awareness representation increases, and if the relative size of the internal structure in the scan image decreases, the node size in the context awareness representation decreases. In this way, there is a direct correlation between the relative sizes of the internal features and the relative sizes of the internal features represented by the nodes.

Furthermore, when the node size of the internal structure decreases below a threshold node size, the respective internal feature may not be indicated in the context awareness representation.

In some examples, when a portion of an internal feature is visible in the scan image, the node size may be based on a relative size of the portion of the internal feature.

As a non-limiting example, if a scan image includes a portion of a first internal feature and a second internal feature, where relative size of the portion of the first internal feature is greater than the second internal feature, the portion of the first internal feature may be represented by a first circular node and the second internal feature may be represented by a second circular node, where a first diameter of the first circular node is greater than a second diameter of the second circular node.

Generating the context awareness representation further includes, at 520, determining a centroid of each node. Determining the centroid of each node may include positioning the respective nodes of each internal feature on the scan image such that the position of the node corresponds to the position of the respective internal feature, and calculating the coordinates of the centroid on the scan image based on a shape of the node.

Upon determining the node sizes and centroids, method 500 proceeds to 522. At 522, method 500 includes displaying each node, and connections between the nodes. In one embodiment, the context awareness graph may be displayed as an overlay with the acquired scan image, where each node is positioned over its respective internal feature and the centroids of each node are connected via one or more segments in such a way that the nodes and the segments indicate a shape of the acquired scan image that is specific to the acquired scan plane. In another embodiment, the context awareness graph may be displayed without underlying scan image.

As a non-limiting example, for an acquired scan image including three internal features and including three nodes as discussed above, the first circular node may be positioned as an overlay over the first internal feature, the second circular node may be positioned as an overlay over the second internal feature, and the third circular node may be positioned as an overlay over the third internal feature on the acquired scan image. A first centroid of the first node may be connected via a first segment with a second centroid of the second node and connected via a second segment with a third centroid of the third node. Further, the second centroid and the third centroids may be connected via a third segment. Thus, the first, second, and third nodes, and the first, second, and third segments together represent a triangular shape of the context awareness graph. The sizes of the nodes represent relative sizes of the internal features in the acquired scan image, and the segments represent relative positions (including an amount of separation between the internal features and an angular position relationship between the internal features, where the amount of separation between the internal features based on the length of the segment) of the internal features in the acquired scan image. Thus, the context awareness graph includes one or more nodes forming one or more vertices of the context awareness graph and one or more segments forming edges of the context awareness graph, each segment connecting at least two nodes; and wherein a number of nodes is based on a number of the one or more anatomical features identified in the scan image. In this way, the context awareness graph including one or more nodes and segments may be presented as an overlay graph on the acquired scan image.

Further, in some embodiments, a threshold node size may be determined, and only those nodes with node size greater than the threshold node size may be displayed.

In this way, a context awareness graph may be generated for a scan image and may provide relative size and position information of one or more internal features captured in the scan image to an operator. Example scan images with context awareness graphs overlays are shown at FIG. 8C.

Further, in one example, as discussed below with respect to FIG. 6, context awareness graph may be generated and displayed in real-time along with the scan image on the user interface of the ultrasound imaging system.

Turning to FIG. 6, an example method 600 for real-time monitoring of current scan image based on real-time generation of context awareness graph is shown. Briefly, real-time monitoring of current scan image may include during a scan, generating a current context awareness graph for each scan image, and may further include determining if a target scan image is achieved based on a comparison of the current context awareness graph of the current scan image and a target context awareness graph of the target scan image. Method 600 may be implemented by one or more of the above disclosed systems, such as image processing system 202 and/or ultrasound system 100, though it should be appreciated that method 600 may be implemented with other systems and components without departing from the scope of the present disclosure.

Method 600 begins at 602. At 602, method 600 includes acquiring the target scan image and generating target context awareness graph for the acquired target scan image. Step 602 may be similar to steps 410 and 412 at FIG. 4.

As discussed above, the target scan image may be selected by an operator from a set of predetermined target scan images stored in the non-transitory memory of the processor. The target scan image may be based on one or more of a type of ultrasound evaluation to be performed, a target scan plane, and a target anatomical feature to be examined. For example, while operating the ultrasound device in a context awareness mode, a user may select the target scan image based on one or more factors indicated above.

Upon acquiring the target scan image, a target context awareness graph may be generated based on the target scan image. The target context awareness graph may indicate relative sizes and relative positions of one or more internal features in the target scan image, where each internal feature is depicted by a node (e.g. circular node), a size of the node based on the relative size of the internal feature, and the positional relationship among the internal features are depicted by one or more segments joining the centroids of each node.

As a non-limiting example, the target scan image may include a right lobe of the liver and a right kidney in a sagittal plane, where the right kidney is positioned at an obtuse angle with respect to the liver. The target context awareness graph may show a first node depicting the kidney and a second node depicting the liver, where a first size (e.g., area) of the first node is less that a second size (e.g., area) of the second node as the relative size of the kidney is less than the liver. Further, a first centroid of the first node is connected to a second centroid of the second node via a segment. The first node is positioned at an obtuse angle with respect to a horizontal reference axis passing through the second centroid of the second node representing the liver. No additional anatomical or internal features are indicated in the example target context awareness graph. In one example, the target context awareness graph may be displayed as an overlay over the target scan image. In other examples, the target context awareness graph may be displayed adjacent to the target scan image. The type of display (overlay or adjacent) of the target awareness graph may be based on the operator selection. An example target context awareness graph displayed as an overlay with the target scan image is shown at FIG. 8C.

Next, at 604, method 600 includes acquiring current scan image based on real-time imaging by the operator, and at 606 method 600 includes generating current context awareness graph for the current scan image. Step 604 and 606 may be similar to steps 418 and 420 at FIG. 4. Briefly, the current context awareness graph may include relative positions and sizes of one or more internal features captured in the current scan image. Continuing the liver and kidney example above, the operator may initiate an ultrasound scan at a scan plane different from the target scan plane. Thus, the current scan image may include three internal features, liver, right kidney, and bowel in contrast to the liver and right kidney features desired (target scan image). Thus, the current context awareness graph includes the first node depicting the kidney, the second node depicting the liver, and a third node (also circular node) depicting the bowel. Further, the first node is at an acute angle with respect to the horizontal reference axis along the centroid of the second node, the third node is an obtuse angle with respect to the horizontal reference axis, and the three nodes are connected at their respective centroids and thus, the current context awareness graph includes a triangular shape with an internal feature at each vertex of the triangle.

Continuing on to 608, method 600 includes displaying the current context awareness graph. As discussed above, the current context awareness graph may be displayed independently at a location (e.g., above, below, or adjacent) not overlapping the current scan image on the user interface, or displayed as an overlay on the current scan image. An example current context awareness graph displayed as an overlay with the current scan image is shown at FIG. 8C.

Next, method 600 includes, at 610, determining if the target scan image is achieved. This includes comparing the target context awareness graph (generated at 602) and the current context awareness graph (generated at 606). The comparison includes comparing a number of nodes, relative sizes of each node, and relative positions of each node between the target context awareness graph and the current context awareness graph. The processor may determine that the target scan image is achieved when the current context awareness graph matches the target context awareness graph. Specifically, the processor may determine that the target scan image is achieved if all of the following is confirmed: 1. a target number of nodes in the target context awareness graph equals the current number of nodes in the current context awareness graph, 2. Size of each node in the target context awareness graph equals (or within an acceptable deviation) size of the corresponding node in the current context awareness graph, and 3. Relative positions (e.g., position of a centroid with respect to a reference axis) of the nodes in the target context awareness graph matches the relative positions of the nodes in the current context awareness graph. Thus, if an overall shape of the target context awareness graph matches the overall shape of the current context awareness graph based on number of nodes, relative sizes and positions of the nodes, the processor may determine that the target scan image is achieved and the target scan plane is achieved.

The determination of whether the target scan image is achieved is further illustrated below using the liver and kidney example discussed above. For example, if the current context awareness graph shows three nodes and the target context awareness graph shows only two nodes, it may be determined that the target scan image is not achieved. However, if the current graph shows two nodes, the processor may go on to determine if the relative sizes and positions of the nodes are within respective threshold limits. For example, it may be determined if an angle between the first centroid (representing kidney) and the reference horizontal axis is equal or within a threshold degree in the target and current context awareness graphs, and if a first node area of the first node and a second node area of the second node is equal or within a threshold area limit in the target and current context awareness graphs. If the answers are yes, the overall shape and size of the target and current context awareness graphs match, and the processor may determine that the target scan image is achieved.

Thus, at 610, if it is confirmed that the target scan image is achieved, method 600 proceeds to 612. At 612, method 600 includes indicating to the user, via the user interface, that the target scan image is achieved. The method may then return to step 426 to display the current and the target context awareness graph as overlays with the current and target scan images or displayed separated from the current and target scan images.

Returning to 610, if it is determined that the current context awareness graph does not match the target context awareness graph, method 600 proceeds to 614. At 614, method 600 includes determining if the current scan plane has changed based on one or more of a probe movement and an indication by the operator. If yes, method 600 returns to 604 and continues to acquire current scan image and update current context awareness graph based on the current scan image until the target scan image is achieved. At 614, if no change to the current scan plane is detected, method 600 includes displaying the current context awareness graph of the current scan image until the change in scan plane is detected. Additionally, method 600 may include, at 616, indicating to the user, via the user interface, that the target scan plane is not achieved.

In this way, a comparison of the current context awareness graph with the target context awareness graph may provide an indication to the user as to whether the target scan image is achieved. While a segmentation graph may include identification of one or more internal features, it may still take numerous trials for the user to determine if the scan is proceeding towards the target scan image or if the user is scanning at the target scan plane. By using the context awareness graph, the user can more efficiently and with increased accuracy evaluate the change in the scan image, and determine if the target scan image is achieved.

Next, FIG. 7 shows an example method 700 for generating one or more desired transformation graphs that indicate a desired change in the context awareness graph of the initial scan image to achieve a desired scan image is shown. Method 700 may be implemented by one or more of the above disclosed systems, such as image processing system 202 and/or ultrasound system 100, though it should be appreciated that method 700 may be implemented with other systems and components without departing from the scope of the present disclosure.

Method 700 begins at 702. At 702, method 700 includes identifying, estimating, and/or measuring one or more target scan image parameters based on a target context awareness graph. Determining the target scan image parameters may include acquiring the target scan image and generating the target context awareness graph as discussed with respect to 410 and 412 of FIG. 4, FIG. 5, and 602 of FIG. 6. The target scan image parameters may be based on one or more internal anatomical features identified in the target scan image and the target context awareness graph, and may include one or more of a number of nodes, relative node size of each node, and relative positions of each node. In some examples, the identity of the one or more internal features may be additionally included as a target scan image parameter.

Continuing on to 704, method 700 include identifying, estimating, and/or measuring one or more initial scan image parameters based on an initial context awareness graph. Determining the initial scan image parameters may include acquiring the initial scan image and generating the initial context awareness graph as discussed with respect to 418 and 420 of FIG. 4, FIG. 5, and 604 and 606 of FIG. 6. The initial scan image parameters may be based on one or more internal anatomical features identified in the initial scan image and the initial context awareness graph, and may include one or more of a number of nodes, relative node size of each node, and relative positions of each node. In some examples, the identity of the one or more internal features may be additionally included as a target scan image parameter.

Further, in some examples, the initial scan image may be indicated by an operator. For example, upon initiating an ultrasound scan and viewing an image of the initial scan, a user may enter the image via a user interface and indicate the image as an initial image for use in the context awareness mode. In some other examples, upon generating a first scan image from the ultrasound scan, the processor may automatically assign the first scan image as the initial scan image. The initial scan image along with the target scan image may then be used as input to determine one or more transformation scan planes as discussed further below.

Next, at 706, method 700 includes comparing values between each corresponding target scan plane parameter and initial scan plane parameter. For example, a number of nodes in the initial context awareness graph may be compared with a number nodes in the target context awareness graph, relative size of each node in the initial graph may be compared with relative size of corresponding nodes in the target graph, and relative angular positions of each node with respect to a reference node or axis in the initial context awareness graph may be compared with relative angular positions of the corresponding nodes in the target graph. Further, identity of each of the internal feature in the initial scan image may be compared with identify of each internal feature in the target scan image. As discussed above, identity of each internal feature in a scan image may be based on a segmentation model, such a CNN model with an autoencoder-autodecoder architecture, as discussed at FIG. 3. Further one or more attributes of the segmentation map of the initial scan image may be abstracted out and entered as inputs into a context awareness module, such as module 209 at FIG. 2, for determining a context awareness graph as discussed with respect to FIG. 5. Furthermore, the process described at FIG. 7 may be carried out by the context awareness module.

Upon comparing the values between each initial scan plane parameter and target scan plane parameter, method 700 includes, at 708, determining a desired direction of probe movement based on the comparison. The desired direction of probe movement may include a desired path from the initial position with respect to the greater human anatomy to a target position with respect to the greater human anatomy. The determination of the desired direction of probe movement may be based on a learnt relationship of a scan plane direction and change in the appearance of anatomical features in a scan image depending on the direction of the scan plane and anatomical position. For example, the context awareness module may be configured to learn relationships between scan plane directionality and changes to relative sizes and relative positions of one or more anatomical features based on the scan plane directionality.

As a non-limiting example, during scanning in a sagittal plane from a superior position to an inferior position with respect to human anatomy, relative size of liver decreases with respect to kidney, and further, relative position of kidney changes with respect to liver. That is, in a scan image captured at a superior position of the human anatomy, size of liver is greater with respect to kidney, and in a scan image captured at a relatively inferior position of the human anatomy, size of liver is smaller with respect to kidney. While the above example illustrates a change in size with respect to probe movement, it will be appreciated that the context awareness module may take into account change in relative positions and appearance/disappearance of one or more features in determining the directionality with respect to the greater human anatomy. Thus, during an ultrasound scan, based on the change in the relative node sizes (node sizes based on relative sizes of the anatomical features) and relative node positions (node positions based on relative positions of the anatomical features), from consecutive scan images for example, the context awareness module may determine direction of probe motion with respect to the greater human anatomy. Further, the context awareness module may be able to locate the scan plane with respect to the greater human anatomy based on the context awareness graph and the scan image.

Further, when the initial scan image parameters (determined from the initial context awareness graph) and the target scan image parameters (determined from the target context awareness graph) are input, the context awareness module may determine which direction to move the probe to achieve the target scan image from the initial scan image.

As another non-limiting example, if an initial scan image includes two anatomical features with size of a first anatomical feature greater than a size of a second anatomical feature (and hence, first node size greater than second node size) and a position of the first anatomical feature at an acute angle with respect to a reference axis, and a target scan image includes the two anatomical features with size of the first anatomical feature smaller than the size of the second anatomical feature (and hence, first node size greater than second node size) and the position of the first anatomical feature is at an obtuse angle with respect to the reference axis, the context awareness module may determine that in order to achieve the target scan image the probe motion may follow an superior to inferior direction based on the learning that when an ultrasound scan proceeds in a superior to inferior direction the first node size decreases with respect to the second node size, and the angle between the first node and the reference axis changes from acute to obtuse.

In this way, based on a learnt relationship between directionality of scan plane and change in relative node size and change in relative positions based on context awareness graphs, a current scan plane with respect to the greater human anatomy may be determined. A non-limiting example illustrating directionality of scan with respect to the greater human anatomy and its relationship is shown at FIG. 10.

Further in addition to relative sizes and relative positions of the representative node, other factors, such as visibility/presence of specific anatomical features in the initial and target scan planes, may also be included in determining the directionality of probe movement.

Continuing on to 710, method 700 includes identifying one or more transformation scan planes in the desired direction of probe movement. The transformation scan planes may be positioned along the desired direction and desired path of probe movement, and may indicate the directionality of desired probe movement.

Upon identifying the one or more transformation scan planes, method 700 includes, at 712 generating and displaying context awareness graphs for each of the one or more transformation scan plane in order to guide the operator from the initial scan plane to the desired scan plane. Generating and displaying the context awareness graphs for the one or more transformation scan planes may include acquiring scan images (from a predetermined set of scan images, for example) for each of the one or more transformation scan planes, and generating transformation context awareness graphs (also referred to herein as desired transformation graphs or desired transformation context awareness graphs) for each of the acquired scan images as discussed at FIG. 5. The transformation context awareness graphs may provide an indication of how the appearance of context awareness graph may change when the probe moves in the desired direction towards the target scan image. The transformation graphs may provide an indication to the operator if the probe is moving in the desired direction towards the target scan image.

In this way, the context awareness graph may be used to determine a probe position with respect to the greater human anatomy and further, provide one or more indications to the operator regarding a desired path of probe motion with respect to the greater human anatomy. For each of the one or more desired transformation scan planes, context generation graphs may be generated and displayed to the user, thereby informing the user a desired change in initial/current context awareness graph to achieve the target scan image. A non-limiting example series of context awareness graphs including an initial context awareness graph, a target context awareness graph, and one or more desired transformation graphs showing desired change in the graphs as the probe moves from the initial scan plane to the desired scan plane is shown at FIG. 9.

FIG. 8A shows a first set of ultrasound images 800 including a first scan image 805 and a second scan image 810. The first scan image 805 may be an initial scan image acquired by an ultrasound sound probe and may include one or more internal features of a patient. The second scan image 810 may be a target scan image, and may include one or more desired internal feature to be examined with respect to the patient during an ultrasound evaluation. In some examples, the target scan image may be selected from a predetermined set of target scan images based on one or more of a target scan plane, one or more desired internal features to be examined, and a desired condition to be evaluated. In other examples, the target scan image may be automatically selected based on one or more inputs including the target scan plane, one or more desired internal features to be examined, and the desired condition entered by the operator. The first and second scan images showing the initial and target scan images are without any annotations or representations, which makes it difficult for an operator to identify the internal features visible in the scan image, determine a current scan plane with respect to the greater human anatomy, and further determine a direction of probe movement and probe position to achieve the target scan image, as shown at 810.

FIG. 8B shows a second set of ultrasound images 815 including a first scan image 820 and a second scan image 830. First and scan images 820 and 830 may be initial and target scan images of FIG. 8A annotated with segmentation graphs with one or more highlights depicting internal features as determined from an output of a segmentation model described with respect to FIG. 3. Specifically, first and second scan images 820 and 830 include highlights 822, 824, and 826 identifying liver, kidney, and bowel respectively. While the second set of images 815 identify the internal features in the scan images, thereby providing anatomy awareness, it will be appreciated that the second set of images 815 do not provide context awareness including relative sizes and relative positions of the internal features in the scan images, and further it may be difficult for an operator to identify the current and target scan planes with respect to the greater human anatomy, and determine a direction of probe movement and its position in order to arrive from the initial scan image, as shown at 820, to the target scan image, as shown at 830.

FIG. 8C shows a third set of ultrasound images 835 including a first scan image 840 and a second scan image 850. The first and second scan images 840 and 850 may be initial and target scan images of FIG. 8B with context awareness representation as determined from an output of the context awareness model described herein. The context awareness representation (also referred to as context awareness graph) may include a first node 842 depicting a first internal feature (which is kidney in this example), a second node 844 depicting a second internal feature (which is liver in this example), and a third node 846 depicting a third internal feature (which is bowel in this example). While the node are represented as circular nodes in this example, other geometric shapes including square, triangle, etc., are within the scope of the disclosure. Further, different nodes may be highlighted with different color schemes for further clarity and ease of identification. Size of each node, which may be an area of the circular node or based on a diameter of the circular node may indicate relative sizes of the internal features in the scan image. For example, the first node 842 has a smaller diameter (and hence, area) with respect to the second node 844, and the third node 846 has a larger diameter with respect to the first node 842 but has a smaller diameter with respect to the second node 844. Thus, in the initial scan plane, as depicted by context awareness graph in 840, the second node 844 is larger than the third node 846 which is larger than the first node 842. At the target scan plane, the relative sizes between the first and the second nodes 842 and 844 are nearly the same or within a threshold difference, however, the third node 846 is not visible.

The context awareness representation further includes, in the initial scan image, a first segment 841 connecting a first centroid of the first node 842 and a second centroid of the second node 844, a second segment 843 connecting the first centroid and a third centroid of the third node 846, and a third segment 845 connecting the third centroid and the first centroid. The connections between the centroids show a positional relationship of the internal features. For example, in the initial scan image, the first node 842 is at an acute angle with respect to a horizontal reference axis passing through the second centroid. In the target scan image, the first node is 842 at an obtuse angle with respect to the horizontal reference axis. Furthermore, the overall shape of the context awareness graph of the initial scan image is a triangle, while the overall shape of the context awareness graph of the target scan image is a segment due to the absence of the third node.

By observing the context awareness graph, the operator may move the probe such that the context awareness graph of the initial scan image starts to change until the current context awareness (generated in real-time based on real-time imaging) resembles the context awareness graph for the target scan image. In some examples, as illustrated below with respect to FIG. 9, and discussed with respect to FIG. 7, one or more transformation graphs may be generated and displayed to the operator to depict the desired changes to the initial scan image to achieve the target scan image. For example, the context awareness module may use, as inputs, the initial context awareness graph of the initial scan image and the target context awareness graph of the target scan image, to determine one or more transformation context awareness graphs and display the transformation graphs to the operator. Furthermore, the context awareness module may determine, based on the initial context awareness graph and the target context awareness graph, a direction of movement of the probe with respect to the greater human anatomy. For example, based on the relative positions of the first node 842 and the second node 844 (from acute angle in the initial graph to obtuse angle in the target graph with respect to the reference axis) in the initial the target context awareness graphs, the context awareness module may determine a desired direction of probe movement (e.g., superior to inferior, dorsal to ventral, etc.) with respect to the greater human anatomy, and indicate the desired direction of probe movement to the operator via the user interface.

Further still, as described with respect to FIG. 11, the context awareness module may continuously monitor the current context awareness graph and compare with the target context awareness graph, and indicate to the user when the current context awareness graph matches the target context awareness graph or if the current context awareness graph deviates from the target context awareness graph by one or more threshold limits (with respect to size, position, number of nodes, etc.).

Referring now to FIG. 11, a flow chart illustrating an example method 1100 for monitoring a current scan image with respect to a target scan image based on the target context awareness graph and the changes to the current context awareness graph in real-time during an ultrasound scan in a context awareness mode is shown. Method 1100 may be implemented by one or more of the above disclosed systems, such as image processing system 202 and/or ultrasound system 100, though it should be appreciated that method 1100 may be implemented with other systems and components without departing from the scope of the present disclosure.

Method 1100 begins at 1102. At 1102, method 1100 includes acquiring a current scan image in real-time based on received information from an ultrasound probe during an ultrasound scan. Next, at 1104, method 1100 includes generating a context awareness graph in real-time based on the current scan image. The context awareness graph may be generated as discussed with respect to FIG. 5, for example.

Next, upon acquiring the current scan image and generating the real-time context awareness graph for the current scan image, method 1100 includes, at 1106, monitoring changes to the current context awareness graph in real-time, which may include comparing current context awareness parameters (determined at time point t) such as node size, relative node positions, and visibility of one or more nodes with the corresponding parameters in the previous context awareness graph (determined at time point t−1). Specifically, monitoring changes to the current context awareness graph in real-time may include, at 1108, monitoring a change in respective node sizes, at 1110, monitoring a change in relative node positions, and at 1112, monitoring visibility of one or more nodes between the current and previous context awareness graphs. Monitoring a change in respective node sizes may include for each node in the current context awareness graph, calculating a change between a current node size and a corresponding node size in the previous context awareness graph. Monitoring a change in relative node positions may include for each node in the current context awareness graph, calculating a change in an angle between the node and a reference axis in the current graph and an angle between the corresponding node and the corresponding reference axis in the previous graph. Monitoring visibility of one or more nodes includes determining if all nodes in the previous graph are present in the current graph and determining if any additional nodes are present or if one or more nodes have disappeared in the current context awareness graph compared to the previous context awareness graph. Further, in some examples, an overall shape of the current context awareness graph may be compared with the previous context awareness graph.

Continuing on to 1114, method 1100 includes determining if each of the changes (that is, differences between the current and the previous context awareness parameters) determined above with respect to step 1106, is proceeding towards the target parameter values. For example, if a first target node size in the target graph is greater than a corresponding first previous node size in the previous graph, the changes may be proceeding towards the target graph if a first current node size (corresponding to the first nodes in the previous and target graphs) is greater than the previous node size. Said another way, if a first node size in current graph is greater than the corresponding first node size in the previous, the changes may be determined to proceed towards the target graph if the first node size in the target graph is greater than current graph. As another example, a current angle between the first node and a reference axis in the current graph is greater than a corresponding angle in the previous graph, it may be determined that the changes are proceeding towards the target graph if the target angle of the first node in the target graph with respect to the reference is greater than the current angle. As a further example, if a target shape of the target graph is a segment and a previous shape of the previous graph is a triangle, the changes may be determined to proceed towards the target graph if a current shape is tending towards a segment.

If it is determined that the changes in real-time are proceeding towards the target context awareness graph, method proceeds to 1116. At 1116, method 1110 includes indicating to a user, via a user interface, that the current scan direction is proceeding towards the target plane. Otherwise, if the change in context awareness parameters are not tending towards the target graph, method proceeds to 1118 to indicate to the user that the current scan is not proceeding towards the target scan plane. Based on these indications, an operator may adjust a scan path of the probe to change the current scan plane and/or a scan direction with respect to the greater human anatomy until the current scan is proceeding towards the target scan plane to achieve the target scan image.

In this way, method 1100 may continue to monitor changes to a current scan image based on the current context awareness graph generated in real time and indicate to a user if the scan direction is proceeding towards the target scan plane to achieve the target scan image. In some examples, based on the changes determined as discussed above, the context awareness module may determine directionality of current scan with respect to greater human anatomy (e.g. superior to inferior, anterior to posterior, etc.), compare with a desired directionality of scan (based on the target context awareness graph) with respect to the greater human anatomy, and indicate to a user a desired direction of probe movement from the current scan plane to achieve the target scan plane.

While the methods at FIGS. 4-7, and 11 are described above with respect to an ultrasound imaging system, it will be appreciated that the context awareness graph may be generated for any medical scan image produced by a medical imaging modality and may include but not limited to imaging systems such as MRI, CT, SPECT, and x-ray imaging systems.

Turning to FIG. 9, a set of context awareness graphs 900 including an initial context awareness graph 910, a target context awareness graph 940, a first transformation graph 920 and a second transformation graph 930 that may be displayed on a user interface, such as interface 115 at FIG. 1 or display device 214 at FIG. 2, is shown. The initial context awareness graph 910 may be based on an initial scan image obtained based on signal from an ultrasound probe, during an ultrasound scan. Further, the target context awareness graph may be based on a selected target scan image. It will be appreciated that depicting a target scan image with context awareness representation may enable a user to select a target scan image. The first and second transformation graphs 920 and 930 may be generated by the processor, as discussed above with respect to FIG. 7. The first and second transformation graphs show desired changes to the initial context awareness graph in order to achieve the target scan image. The initial and target context awareness graphs 910 and 940 are similar to the initial and target context awareness graphs overlaid on initial and target scan images shown at 840 and 850 of FIG. 8 respectively, and hence are similarly numbered. For the sake of brevity, description of similarly numbered features are omitted here. While the present example depicts only context awareness graphs, it will be appreciated that the context awareness graphs may be displayed to the operator as one or more of overlays on the corresponding scan images, as shown at FIG. 8, context awareness graphs without the scan images, as shown here at FIG. 9, and adjacently positioned with respect to the scan images (not shown).

As depicted at 910, the initial context awareness graph 910 shows a triangular shape of the initial context awareness graph including three nodes, and the first node 842 is at an acute angle θ1 with respect to a reference axis 912 that passes through a centroid of the second node 844. However, the target context awareness graph 940 shows a segment instead of the overall triangular shape, and first node 842 is at an obtuse angle θ4 with respect to the reference axis 912. Based on the initial graph parameters and the target graph parameters including node size, node position, and number of nodes, the first and second transformation context awareness graphs 920 and 930 may be displayed to the user depicting how the subsequent context awareness graphs, following the initial graph, may appear when the scan proceeds in a direction towards the target scan image. For example, when the scan proceeds in the direction towards the target scan image, the angle θ1 may increase to θ2 at 920 and further increase to θ3 at 930 until target angle θ4 is achieved. The change in relative position of the first node with respect to the reference axis indicates the desired change in relative position of the internal feature represented by the first node. Further, the processor may map the desired change in the initial context awareness graph with respect to the grater human anatomy and indicate a desired direction of movement of the probe. In the present example, the processor may determine that in order to achieve the target scan image from the initial scan plane via the first and second transformation scan planes, the probe may move towards an anterior direction from an initial position with respect to the grater human anatomy. A non-limiting example mapping the changes to context awareness parameters node size and relative node positions, with respect to greater human anatomy is illustrated with respect to FIG. 10.

Turning to FIG. 10, graphs 1000 and 1050 show a non-limiting example illustrating changes in relative sizes and positions of one or more nodes in the context of greater human anatomy. Specifically, graphs 1000 and 1050 show changes in relative sizes and relative position, respectively, of a first internal feature with respect to a second internal feature as the ultrasound probe moves in the anterior/superior to posterior/inferior direction of the human body.

The change in relative size of the first internal feature with respect to the second internal feature as the scan proceeds from anterior to posterior direction with respect to the human anatomy may be depicted by 1010. Specifically, the change in relative size of the internal features is depicted based on change in node size. Thus, Y axis indicates size of first node representing the first internal feature with respect to the size of second node representing the second internal feature, and X-axis indicates a direction of probe movement with respect to the greater human anatomy. A current relative size is indicated at 1020, an initial relative size is indicated at 1030, and a target relative size is indicated at 1040. Based on the graph 1010, the current size has increased with respect to the initial size, and thus indicates a probe movement from the posterior to anterior direction. However, the desired direction of probe movement, based on the initial size and the target size, may be in the anterior to posterior direction such that the relative size decreases. Thus, based on the initial, current, and target size of the first and second nodes, the processor may map the current position/current scan plane with respect to the greater human anatomy, and provide one or more indications to the user including a desired direction of probe movement to achieve the target scan plane, an expected (desired) change in node sizes in the desired direction of probe movement, and expected (desired) changes to an overall shape of the initial context awareness graph, the initial graph based on the initial scan image at the initial scan plane to achieve the target context awareness map based on the target scan image at the target scan plane.

An example change in relative position of the first internal feature with respect to the second internal feature as the scan proceeds from anterior to posterior direction with respect to the human anatomy is depicted by 1090. Specifically, the change in relative positions of the internal features is depicted based on change in an angular position of the first internal feature with respect to a reference axis passing through the second internal feature. Thus, Y axis indicates angular position of the first node representing the first internal feature with respect to the angular position of the second node representing the second internal feature, where the angular position increases from acute to obtuse angle in the direction of y-axis, and X-axis indicates a direction of probe movement with respect to the greater human anatomy. Similar to graph 1000, current, initial, and target positions are indicated by 1060, 1070, and 1080 respectively.

As indicated by 1090, in order to achieve the target angular position, depicted at 1080, the probe may be moved from an anterior to posterior direction such that the relative angle decreases from the initial to target positions. However, as the current position indicates an increase in relative angular position, it may be inferred that from the initial scan plane to the current scan plane, the probe has moved in a direction opposite to the desired direction, and as such, the processor may provide an indication to the operator to move the probe towards the posterior direction with respect to greater human anatomy to achieve the target relative position.

Thus, as discussed with respect to relative node size, based on the initial, current, and target angular positions of the first and second nodes, the processor may map the current position/current scan plane with respect to the greater human anatomy, and provide one or more indications to the user including a desired direction of probe movement to achieve the target scan plane, an expected (desired) change in relative node positions in the desired direction of probe movement, and expected (desired) changes to an overall shape of the initial context awareness graph, the initial graph based on the initial scan image at the initial scan plane to achieve the target context awareness map based on the target scan image at the target scan plane. Taken together, any scan image of a scan plane may be used to generate a context awareness graph based on segmentation data of the scan image. The context awareness graph may include one or more nodes representing one or more internal anatomical features in the scan image and forming one or more vertices of the context awareness graph, and further include one or more segments forming edges of the context awareness graph, each segment connecting at least two nodes, wherein a number of nodes is based on a number of the one or more internal anatomical features identified in the scan image. Further, a context awareness with respect to the greater human anatomy may be determined based on a current or initial context awareness graph and a target context awareness graph.

A technical effect of generating and displaying context awareness annotations on identified anatomical internal features of a medical scan image may include a real-time visual feedback to an operator performing a medical scan to indicate a current scan plane and guide the operator towards a target scan plane. As a result, reliance on sensor based systems (e.g., for haptic feedback) that are coupled to the medical device, such as an ultrasound probe, is reduced. This in turn, reduces manufacturing and maintenance costs, while improving accuracy and efficiency. A technical effect of generating and displaying context awareness annotations on identified anatomical internal features further includes real-time awareness of current scan plane with respect to the target scan plane in the context of greater human anatomy. As a result, the user may arrive at the target scan plane more quickly, and further identify the target plane which may otherwise be difficult to discern, due to poor resolution, inexperience, etc. Consequently, the medical scan may be performed with increased accuracy and improved efficiency.

An embodiment for a method for a medical imaging processor includes acquiring a medical scan image; identifying one or more internal features in the medical scan image; generating a context awareness graph based on relative sizes and relative positions of the one or more internal features; and displaying the context awareness graph on a display portion of a user interface communicatively coupled to the medical imaging processor; wherein the context awareness graph includes a relative position annotation and a relative size annotation for each of the one or more internal features identified in the medical scan image.

A first example of the method includes wherein identifying the one or more internal features is based on a segmentation model; and wherein generating the context awareness graph includes isolating relative size and relative position attributes for each of the one or more internal features from an output of the segmentation model. In a second example of the method, which optionally includes the first example, and further includes wherein generating the context awareness graph includes depicting each of the one or more internal features by a node, where a size of each node is based on the relative sizes of the one or more internal features. In a third example of the method, which optionally includes one or both of the first and second examples, the method further includes wherein generating the context awareness graph includes determining a centroid for each node and depicting relative positions of each node by one or more segments connecting the centroids of each node. In a fourth example of the method, which optionally includes one or more or each of the first through third examples, the method further includes wherein an overall shape of the context awareness graph is based on the relative positions of the one or more internal features. In a fifth example of the method, which optionally includes one or more or each of the first through fourth examples, the method further includes wherein the acquired medical scan image is based on ultrasound signal data received from an ultrasound probe during an ultrasound scan. In a sixth example of the method, which optionally includes one or more or each of the first through fifth examples, the method further comprises selecting a target scan image from a set of predetermined scan images stored in a non-transitory memory; generating a target context awareness graph of the target scan image based on one or more target internal features identified in the target scan image; and determining a desired direction of ultrasound probe movement with respect to a human anatomy based on the context awareness graph and the target context awareness graph; wherein the target awareness graph includes a second relative position annotation and a second relative size annotation for each of the one or more target internal features identified in the target scan image. In a seventh example of the method, which optionally includes one or more or each of the first through sixth examples, the method further includes displaying the context awareness graph, the target context awareness graph; and the desired direction of ultrasound probe movement on the display portion of the user interface.

An embodiment is directed to a method for a medical imaging processor, comprising, during an ultrasound scan, acquiring a current scan image, the current scan image based on real-time scan data from an ultrasound probe; identifying one or more anatomical features in the current scan image based on a segmentation model; isolating one or more attributes of each of the one or more internal features based on an output of the segmentation model, the one or more attributes including a size information and a position information for each of the one or more anatomical features; generating a current context awareness graph based on the one or more isolated attributes; and displaying the current context awareness graph on a display portion of a user interface coupled to the processor; wherein the current context awareness graph includes a first annotation and a second annotation for each of the one or more internal features; and wherein the first annotation is based on relative sizes of each of the one or more internal features, and the second annotation is based on relative positions of each of the one or more internal features. A first example of the method includes wherein the first annotation includes a node representing each of the one or more internal features, each node having a geometric shape and a size of each node based on a size of corresponding internal feature relative to size of one or more other internal features in the current scan image. In a second example of the method, which optionally includes the first example, the second annotation includes a segment joining at least two nodes at their respective centroids, a length of each segment based on a distance between two corresponding internal features represented by the two nodes; and an angle between the segment and a reference axis is based on relative positions of the two corresponding internal features. In a third example of the method, which optionally includes one or both of the first and second examples, the method further includes during the ultrasound scan, selecting a target scan image, the target scan image selected from a set of predetermined target scan images; and wherein the target scan image based on one or more of a target scan plane, one or more desired anatomical features for ultrasound evaluation, and a medical condition to be evaluated during the scan. In a fourth example of the method, which optionally includes one or more or each of the first through third examples, the method further comprises determining one or more transformation scan planes based on the current and target context transformation graphs; identifying one or more transformation scan images based on the transformation scan planes; generating one or more transformation context awareness graphs based on the one or more transformation scan images; and displaying the one or more context awareness graphs on the display portion; wherein determining one or more transformation scan planes is based on a desired direction of probe movement based on the current and target transformation graphs. In a fifth example of the method, which optionally includes one or more or each of the first through fourth examples, determining one or more transformation scan planes includes determining a current scan plane with respect to greater human anatomy based on the current and target context awareness graphs. In a sixth example of the method, which optionally includes one or more or each of the first through fifth examples, the method further includes comprising displaying the desired direction of probe movement on the display portion.

An embodiment for an imaging system is provided. The imaging system includes an ultrasound probe; a user interface including a display portion; and a processor configured with instructions in non-transitory memory that when executed cause the processor to acquire an ultrasound scan image generated based on scan data from the ultrasound probe; identify one or more anatomical features present in the ultrasound scan image based on a first model; determine one or more context awareness parameters for each of the one or more anatomical features from an output of the first model; generate a context awareness graph for the ultrasound scan image based on the one or more context awareness parameters; and display the context awareness graph on the display portion; and wherein the one or more context awareness parameters includes relative sizes and relative positions of each of the one or more anatomical features. In a first example of the imaging system, the context awareness graph includes one or more nodes forming one or more vertices of the context awareness graph and one or more segments forming edges of the context awareness graph, each segment connecting at least two nodes; and wherein a number of nodes is based on a number of the one or more anatomical features identified in the scan image. In a second example of the imaging system, which optionally includes the first example, each node represents each of the one or more anatomical features; wherein a size of each node is based on a relative size of the corresponding anatomical feature; and wherein an arrangement of the one or more nodes is based on the relative positions of the one or more anatomical features. In a third example of the imaging system, which optionally includes one or both of the first and second examples, a number of nodes is further based on a node size greater than a threshold. In a fourth example of the imaging system, which optionally includes one or more or each of the first through third examples, the processor further includes instructions to acquire a target scan image, the target scan image selected from a set of predetermined target scan images stored in non-transitory memory; generate a target context awareness graph based on the target scan image; compare the current context awareness graph and the target context awareness graph; and provide an indication, via the display portion, that the target scan image is achieved when the number of nodes in the context awareness graph is same as a target number of nodes in the target awareness graph; the size of each node in the current context awareness graph is within a threshold limit with respect to size of each corresponding node in the target context awareness graph; and an overall shape of the context awareness graph matches an overall target shape of the target context awareness graph.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for a medical imaging processor, comprising:
   acquiring a medical scan image;
   identifying one or more internal features in the medical scan image;
   generating a context awareness graph based on relative sizes and relative positions of the one or more internal features, including depicting each of the one or more internal features by a node, where a size of each node is based on the relative sizes of the one or more internal features, determining a centroid for each node, and depicting relative positions of each node by one or more segments connecting the centroids of each node; and
   displaying the context awareness graph on a display portion of a user interface communicatively coupled to the medical imaging processor;
   wherein the context awareness graph includes a relative position annotation and a relative size annotation for each of the one or more internal features identified in the medical scan image.

2. The method of claim 1, wherein identifying the one or more internal features is based on a segmentation model; and wherein generating the context awareness graph includes isolating relative size and relative position attributes for each of the one or more internal features from an output of the segmentation model.

3. The method of claim 1, wherein an overall shape of the context awareness graph is based on the relative positions of the one or more internal features.

4. The method of claim 1, wherein the acquired medical scan image is based on ultrasound signal data received from an ultrasound probe during an ultrasound scan.

5. The method of claim 4, further comprising selecting a target scan image from a set of predetermined scan images stored in a non-transitory memory; generating a target context awareness graph of the target scan image based on one or more target internal features identified in the target scan image; and determining a desired direction of ultrasound probe movement with respect to a human anatomy based on the context awareness graph and the target context awareness graph; wherein the target context awareness graph includes a second relative position annotation and a second relative size annotation for each of the one or more target internal features identified in the target scan image.

6. The method of claim 5, further comprising displaying the context awareness graph, the target context awareness graph, and the desired direction of ultrasound probe movement on the display portion of the user interface.

7. A method for a medical imaging processor, comprising:
   during an ultrasound scan,
      acquiring a current scan image, the current scan image based on real-time scan data from an ultrasound probe;
      identifying one or more internal features in the current scan image based on a segmentation model;
      isolating one or more attributes of each of the one or more internal features based on an output of the segmentation model, the one or more attributes including a size information and a position information for each of the one or more internal features;
      generating a current context awareness graph based on the one or more isolated attributes; and
      displaying the current context awareness graph on a display portion of a user interface coupled to the medical imaging processor;
   wherein the current context awareness graph includes a first annotation and a second annotation for each of the one or more internal features; and
   wherein the first annotation is based on relative sizes of each of the one or more internal features, and the second annotation is based on relative positions of each of the one or more internal features, wherein the first annotation includes a node representing each of the one or more internal features, each node having a geometric shape and a size of each node based on a size of corresponding internal feature relative to a size of one or more other internal features in the current scan image, wherein the second annotation includes a segment joining at least two nodes at their respective centroids, a length of each segment based on a distance between at least two corresponding internal features represented by the at least two nodes, and wherein an angle between the segment and a reference axis is based on relative positions of the at least two corresponding internal features.

8. The method of claim 7, further comprising during the ultrasound scan, selecting a target scan image and generating a target context awareness graph based on the target scan image, the target scan image selected from a set of predetermined target scan images; and wherein the target scan image is based on one or more of a target scan plane, one or more desired anatomical features for ultrasound evaluation, and a medical condition to be evaluated during the scan.

9. The method of claim 8, further comprising determining one or more transformation scan planes; identifying one or more transformation scan images based on the one or more transformation scan planes; generating one or more transformation context awareness graphs based on the one or more transformation scan images; and displaying the one or more transformation context awareness graphs on the display portion; wherein determining the one or more transformation scan planes is based on a desired direction of probe movement based on the current context awareness graph and target context awareness graph.

10. The method of claim 9, wherein determining the one or more transformation scan planes includes determining a current scan plane based on the current and target context awareness graphs.

11. The method of claim 9, further comprising displaying the desired direction of probe movement on the display portion.

12. An imaging system, comprising:
an ultrasound probe;
a user interface including a display portion; and
a processor configured with instructions in non-transitory memory that when executed cause the processor to:
acquire an ultrasound scan image generated based on scan data from the ultrasound probe;
identify one or more anatomical features present in the ultrasound scan image based on a first model;
determine one or more context awareness parameters for each of the one or more anatomical features from an output of the first model, wherein the one or more context awareness parameters includes relative sizes and relative positions of each of the one or more anatomical features;
generate a context awareness graph for the ultrasound scan image based on the one or more context awareness parameters, the context awareness graph including one or more nodes;
display the context awareness graph on the display portion;
acquire a target scan image, the target scan image selected from a set of predetermined target scan images stored in non-transitory memory;
generate a target context awareness graph based on the target scan image;
compare the context awareness graph and the target context awareness graph; and
provide an indication, via the display portion, that the target scan image is achieved when a number of nodes in the context awareness graph is same as a target number of nodes in the target context awareness graph; a size of each node in the context awareness graph is within a threshold limit with respect to a size of each corresponding node in the target context awareness graph; and an overall shape of the context awareness graph matches an overall target shape of the target context awareness graph.

13. The system of claim 12, wherein the one or more nodes of the context awareness graph form one or more vertices of the context awareness graph and one or more segments of the context awareness graph form edges of the context awareness graph, each segment connecting at least two nodes; and wherein the number of nodes of the context awareness graphs is based on a number of the one or more anatomical features identified in the ultrasound scan image.

14. The system of claim 13, wherein each node of the context awareness graph represents each of the one or more anatomical features; wherein a size of each node of the context awareness graph is based on a relative size of a corresponding anatomical feature; and wherein an arrangement of the one or more nodes of the context awareness graph is based on the relative positions of the one or more anatomical features.

15. The system of claim 14, wherein the number of nodes of the context awareness graphs is further based on a node size greater than a threshold.

* * * * *